US008227587B2

(12) United States Patent  (10) Patent No.: US 8,227,587 B2
Quentin-Millet  (45) Date of Patent: Jul. 24, 2012

(54) DENGUE CHIMERIC VIRUSES

(75) Inventor: Marie-Jose Quentin-Millet, Lyons (FR)

(73) Assignee: Sanofi Pasteur SA, Lyons (FR)

( * ) Notice: Subject to any disclaimer, the term of this patent is extended or adjusted under 35 U.S.C. 154(b) by 4 days.

(21) Appl. No.: 13/102,685

(22) Filed: May 6, 2011

(65) Prior Publication Data

US 2011/0206730 A1   Aug. 25, 2011

Related U.S. Application Data

(62) Division of application No. 11/619,687, filed on Jan. 4, 2007, now Pat. No. 7,968,102.

(60) Provisional application No. 60/863,708, filed on Jan. 13, 2006.

(51) Int. Cl.
*C07H 21/00* (2006.01)
*A61K 39/12* (2006.01)

(52) U.S. Cl. .............. 536/23.72; 424/199.1; 424/218.1; 435/69.1; 435/71.1; 435/235.1; 435/325

(58) Field of Classification Search ........................ None
See application file for complete search history.

(56) References Cited

U.S. PATENT DOCUMENTS 7,641,907 B2   1/2010   Kinney et al.

FOREIGN PATENT DOCUMENTS

| EP | 1159968 A1 | 5/2001 |
|----|-----------|--------|
| WO | 93/06214 A1 | 4/1993 |

OTHER PUBLICATIONS

Dunnen, et al., "Mutation Nomenclature Extensions and Suggestions to Describe Complex Mutations: A Discussion," Human Mutation, 2000, pp. 7-12, vol. 15, Wiley-Liss, Inc.
Freestone, D.S., "Yellow Fever Vaccine," Vaccines, 1995, pp. 741-779, second edition, W. B. Saunders, PA.
Gubler, D. J., et al., "Dengue and Dengue Hemorrhagic Fever," 1997, pp. 1-22, CABI International Publishing.
Huang Claire Y., et al., "Chimeric Dengue Type 2 (Vaccine Strain PDK-53)/Dengue Type 1 Virus as a Potential Candidate Dengue Type 1 Virus Vaccine," Journal of Virology, Apr. 2000, pp. 3020-3028, vol. 74, No. 7, American Society for Microbiology.
Kautner, Ingrid, et al., "Dengue Virus Infection: Epidemiology, Pathogenesis, Clinical Presentation, Diagnosis, and Prevention," Journal of Pediatrics, Oct. 1997, pp. 516-524, vol. 131, No. 4.
Peyrefitte, Christophe N., "Genetic Characterization of Newly Reintroduced Dengue Virus Type 3 in Martinique (French West Indies)," Journal of Clinical Microbiology, Nov. 2003, pp. 5195-5198, vol. 41, No. 11, American Society for Microbiology.
Pugachev, Konstantin V., et al., "High Fidelity of Yellow Fever Virus RNA Polymerase," Journal of Virology, Jan. 2004, pp. 1032-1038, vol. 78, No. 2, American Society for Microbiology.
Rice, Charles M., et al., "Nucleotide Sequence of Yellow Fever Virus: Implications for Flavivirus Gene Expression and Evolution," Science, Aug. 23, 1985, pp. 726-733, vol. 229.
Rigau-Perez, Jose G., et al., "Dengue and Dengue Haemorrhagic Fever," The Lancet, Sep. 19, 1998, pp. 971-977, vol. 352.
Rothman, Alan, et al., "Immunopathogenesis of Dengue Hemorrhagic Fever," Virology, 1999, pp. 1-6, vol. 257.
International Search Report for PCT/EP2007/050290 mailed May 7, 2007.
Butrapet, et al., "Attenuation Markers of a Candidate Dengue Type 2 Vaccine Virus, Strain 16681 (PDK-53), are Defined by Mutations in the 5' Noncoding Region and Nonstructural Proteins 1 and 3," Journal of Virology, Apr. 2000, p. 3011-3019, vol. 74, No. 7, American Society for Microbiology.
Guirakhoo, et al., "Recombinant Chimeric Yellow Fever-Dengue Type 2 Virus is Immunogenic and Protective in Nonhuman Primates," Journal of Virology, Jun. 2000, p. 5477-5485, vol. 74, No. 12, American Society for Microbiology.
International Preliminary Report on Patentability for PCT/EP2007/050290 issued Jul. 15, 2008.
Gubler, D.J., "Dengue," The Arboviruses: Epidemiology and Ecology, 1988, pp. 223-260, vol. 2.
Sabin, Albert B., "Research on Dengue During World War II," The American Journal of Tropical Medicine an Hygiene, 1952, pp. 30-50, vol. 1, The Williams and Wilkins Company.
Smithburn, Kenneth C., et al., "Immunology of Yellow Fever,"Yellow Fever Vaccination, World Health organization Monograph Series, 1956, pp. 1-238.
Vaughn, David W., et al., "Dengue in the Early Febrile Phase: Viremia and Antibody Response," Journal of Infectious Diseases, 1997, pp. 322-330, vol. 176, The University of Chicago.
Vaughn, David W., et al., "Dengue Viremia Titer, Antibody Response Pattern, and Virus Serotype Correlate With Disease Severity," Journal of Infectious Diseases, 2000, pp. 2-9, vol. 181, Infectious Diseases Society of America.
"WHO Technical Guide," Dengue Haemorrhagic Fever: Diagnosis, Treatment and Control, 1986, pp. 1-58, World Health Organization, Geneva.
Wu, Shuenn-Jue L., "Human Skins Langerhans Cells Are Targets of Dengue Virus Infection," Nature Medicine, Jul. 2000, pp. 816-820, vol. 6, No. 7.

*Primary Examiner* — Stacy B. Chen
(74) *Attorney, Agent, or Firm* — McDonnell Boehnen Hulbert & Berghoff LLP

(57) ABSTRACT

The invention relates to Dengue chimeric viruses which are less prone to accumulate point mutations and genetic variations. In these Dengue chimeric viruses, the NS5 gene, which encodes polymerase, has been replaced by the corresponding NS5 sequence of a Yellow Fever virus.

9 Claims, 5 Drawing Sheets

DENGUE CHIMERIC VIRUSES

This application claims the benefit of priority of U.S. provisional application 60/863,708, filed Jan. 13, 2006.

BACKGROUND OF THE INVENTION

1. Field of the Invention

The invention relates to Dengue chimeric viruses of high genetic stability which are thus less prone to revert to a non-attenuated phenotype. In these dengue chimeric viruses, the NS5 sequence, which encodes polymerase, has been replaced by the corresponding NS5 sequence of a Yellow Fever virus.

2. Summary of the Related Art

Dengue disease is the second most important tropical infectious disease after malaria, with over half of the world's population (2.5 billion) living in areas at risk for epidemic transmission. An estimated 50 to 100 million cases of Dengue, 500,000 hospitalised DHF patients and 25,000 deaths occur each year. Dengue is endemic in Asia, the Pacific, Africa, Latin America, and the Caribbean.

Dengue haemorrhagic fever (DHF) is a severe febrile disease characterised by abnormalities of homeostasis and increased vascular permeability that can lead to hypovolemia and hypotension (Dengue shock syndrome, DSS) often complicated by severe internal bleeding. The case fatality rate of DHF can be as high as 10% without therapy, but below 1% in most centres with therapeutic experience (WHO Technical Guide, 1986).

Dengue diseases are caused by four closely related, but antigenically distinct, virus serologic types (Gubler, 1988; Kautner et al., 1997; Rigau-Pérez et al., 1998; Vaughn et al., 1997), of the genus Flavivirus (Gubler, 1988). Infection with a Dengue virus serotype can produce a spectrum of clinical illnesses ranging from a non-specific viral syndrome to severe, fatal haemorrhagic disease. The incubation period of Dengue fever (DF) after the mosquito bite averages 4 days (range 3-14 days). DF is characterised by biphasic fever, headache, pain in various parts of the body, prostration, rash, lymphadenopathy and leukopenia (Kautner et al., 1997; Rigau-Pérez et al., 1998). The viremic period is the same as of febrile illness (Vaughn et al., 1997). Recovery from DF is usually complete in 7 to 10 days but prolonged asthenia is common. Leukocytes and platelets counts decreases are frequent.

The viruses are maintained in a cycle that involves humans and *Aedes aegypti*, a domestic, day-biting mosquito that prefers to feed on humans. Human infection is initiated by the injection of virus during blood feeding by an infected *Aedes aegypti* mosquito. Salivary virus is deposited mainly in the extravascular tissues. The primary cell subset infected after inoculation is dendritic cells, which subsequently migrate to draining lymph nodes (Wu et al., 2000). After initial replication in the skin and draining lymph nodes, virus appears in the blood during the acute febrile phase, generally for 3 to 5 days.

Monocytes and macrophages are with dendritic cells among the primary target of dengue virus. Protection against homotypic reinfection is complete and probably lifelong, but cross-protection between dengue types lasts less than 12 weeks (Sabin, 1952). Consequently a subject can experience a second infection with a different serotype. A second dengue infection is a theoretical risk factor of developing severe dengue disease. However, DHF is multifactorial including: the strain of the virus involved, as well as the age, immune status, and genetic predisposition of the patient. Two factors play a major role in the occurrence of DHF: a rapid viral replication with high viremia (the severity of the disease being related to the level of viremia (Vaughn et al., 2000) and an important inflammatory response with release of high levels of inflammatory mediators (Rothman and Ennis, 1999).

There is no specific treatment against Dengue diseases. The management of DF is supportive with bed rest, control of fever and pain with antipyretics and analgesics, and adequate fluid intake. The treatment of DHF needs correction of fluid loss, replacement of coagulation factors, and infusion of heparin.

Preventive measures presently rely on vector control and personal protection measures, which are difficult to enforce and expensive. No vaccine against Dengue is currently registered. Since the 4 serotypes of dengue are circulating worldwide and since they are reported to be involved in cases of DHF, vaccination should ideally confer protection against all 4 dengue virus serotypes.

Live attenuated vaccines (LAVs), which reproduce natural immunity, have been used for the development of vaccines against many diseases. The advantages of live-attenuated virus vaccines are their capacity of replication and induction of both humoral and cellular immune responses. In addition, the immune response induced by a whole virion vaccine against the different components of the virus (structural and non-structural proteins) reproduced those induced by natural infection.

A dengue vaccine project was initiated in Thailand at the Centre for Vaccine Development, Institute of Sciences and Technology for Development Mahidol University. Candidate live-attenuated vaccines were successfully developed, at a laboratory scale, for dengue serotypes 1 to 4. These vaccines have been tested as monovalent (single serotype), bivalent (two serotypes), trivalent (three serotypes), and tetravalent (all four serotypes) vaccines in That volunteers. Those vaccines were found to be safe and immunogenic in children and in adults (Gubler, 1997). However, these LAV strains correspond to heterogeneous populations and represent a risk due to a potential in vitro or in vivo selection of one of the strain present in the composition. Indeed, dengue viruses are prone to generate mutations and genetic variations during their replication process.

Pugachev et al. (2004) have recently published that the polymerase encoded by the NS5 gene of the Yellow Fever virus is characterized by a greater fidelity as compared to other flaviviruses.

SUMMARY OF THE INVENTION

The inventors use the unique features of the Yellow Fever polymerase to construct chimeric recombinant Dengue viruses wherein the original polymerase encoding sequence is replaced by the corresponding sequence of a Yellow Fever strain thus leading to live attenuated dengue viruses of higher genetic stability which would represent useful vaccine candidates.

DETAILED DESCRIPTION OF THE INVENTION

Definitions

Figure 1:
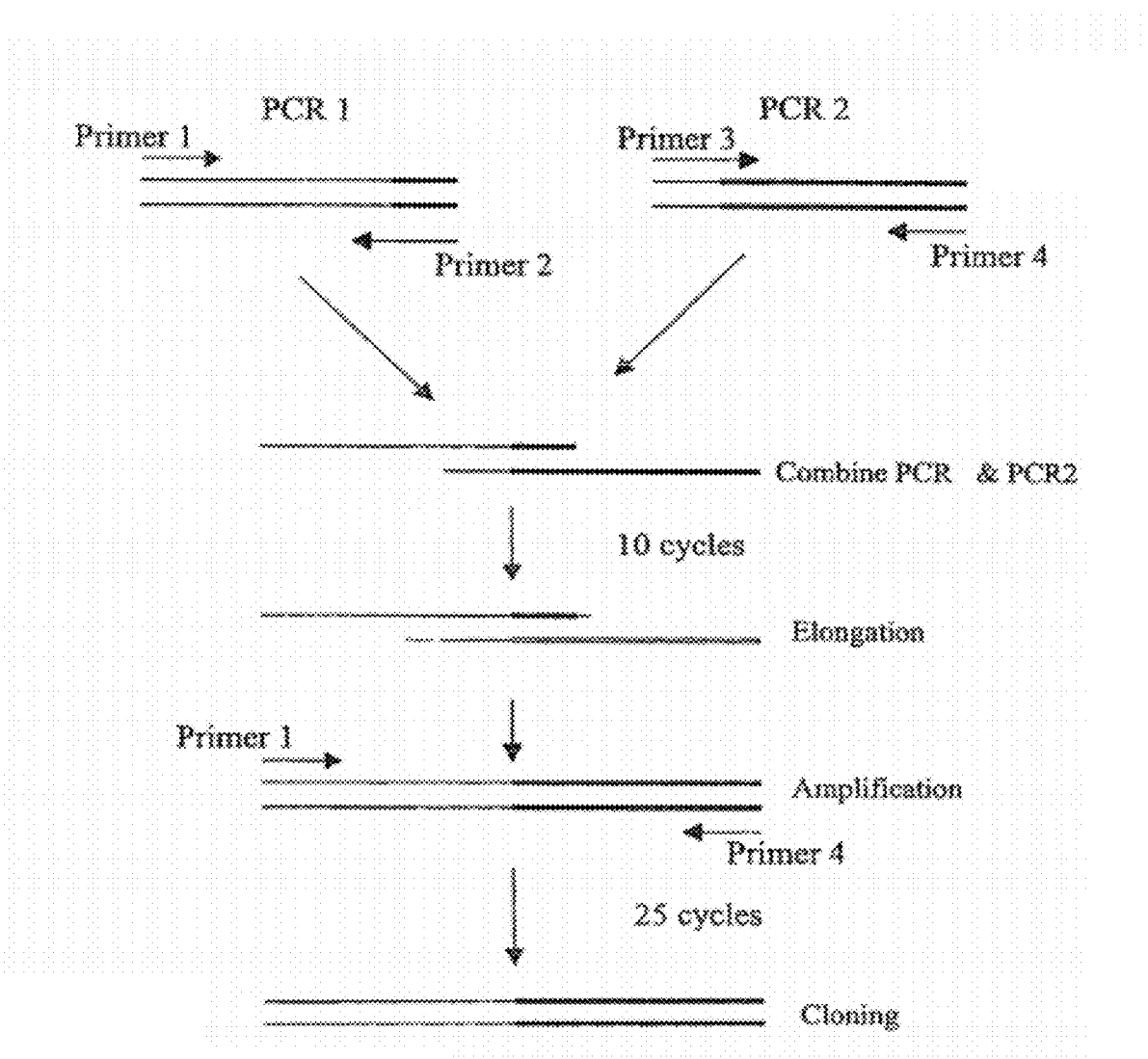
FIG. 1 is a diagrammatic representation of the three steps PCR strategy which can be used to construct a chimeric Dengue 3 virus containing the Yellow Fever NS5 sequence.
Figure 2:
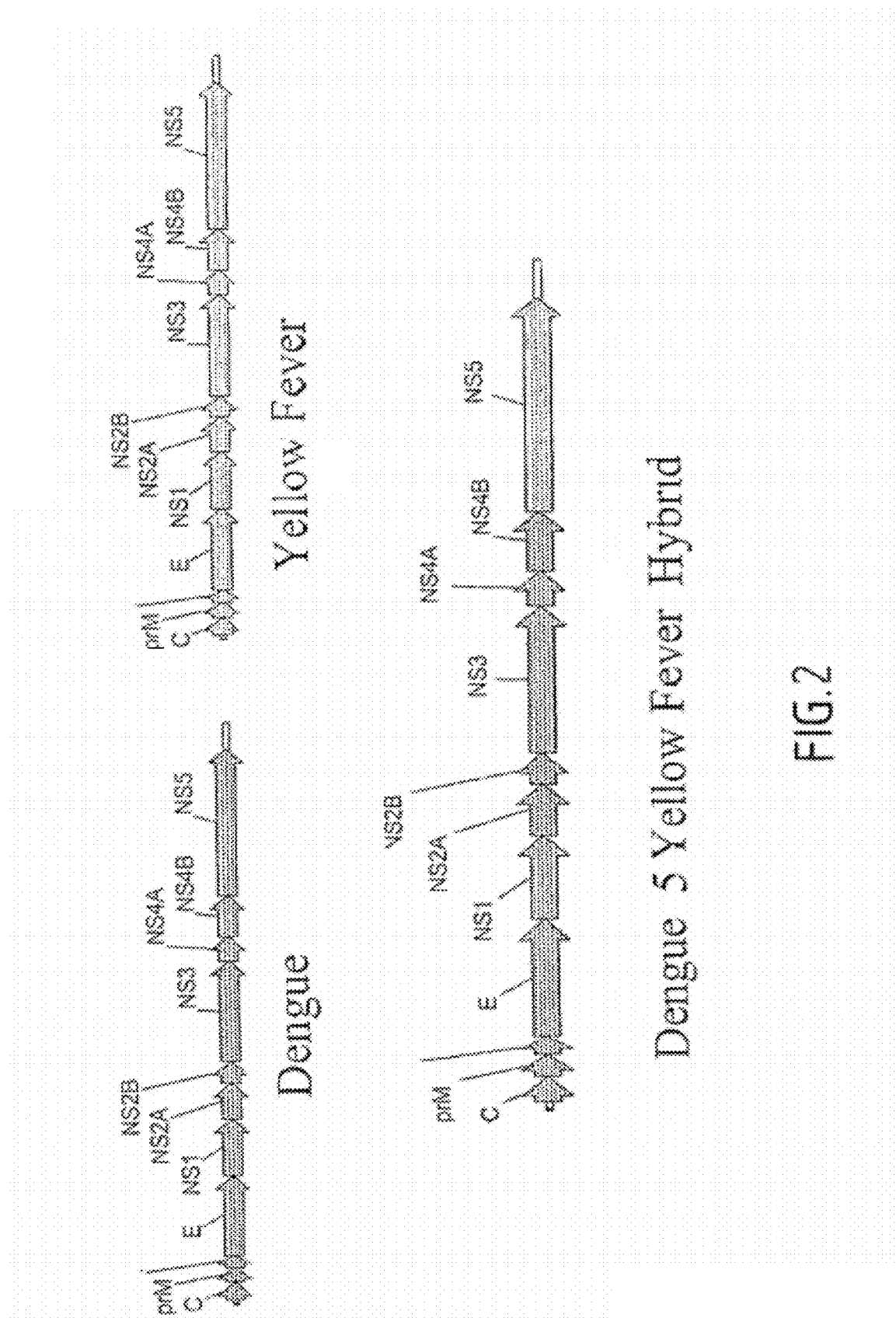
FIG. 2 is a diagrammatic representation of the genomic organization of Dengue virus and Yellow Fever virus, and of the chimeric Dengue 3/Yellow Fever virus.

By the expression "Yellow Fever strain", we mean here any Yellow Fever Strain. As a matter of example a YFD17 strain can be used. This strain has been described by Smithburn et al. (1956) and by Freestone (1995). YF17D has also been studied at the genetic level (Rice et al., 1985) and its genomic sequence is shown in SEQ ID No.7 (Genbank accession number NC 002031). Indeed in the context of the present invention, the NS5 sequence to be inserted in the dengue virus can originate from any Yellow Fever Strain. In one embodiment of the invention, the NS5 encoding sequence of a Dengue virus is replaced by the corresponding NS5 encoding sequence of the YFD 17 strain. Advantageously, the 3'NCR sequence of the same Dengue virus is also replaced by the corresponding 3'NCR sequence of the same Yellow Fever strain.

As used herein, a Dengue (DEN) virus denotes a wild-type Dengue virus of serotype 1, 2, 3 or 4, or a live attenuated Dengue viral strain of serotypes 1, 2, 3, or 4. Dengue viruses are RNA viruses presenting the following gene organization: 5'-noncoding region (NCR), structural protein (capsid (C), premembrane/membrane (prM/M), envelope (E)) and non structural protein (NS1-NS2A-NS2B-NS3-NS4A-NS4B-NS5) and 3' NCR. The RNA genome is associated with the C proteins to form nucleotide (icosadedral symmetry). As with other flaviviruses, the DEN viral genome encodes an uninterrupted open reading frame (ORF) which is translated to a single polyprotein.

In particular, a Dengue serotype 1 (DEN-1) virus may be the wild-type strain 16007. A Dengue serotype 2 (DEN-2) virus may be the wild-type strain 16681. A Dengue serotype 3 (DEN-3) virus may be the wild-type strain 16562 or the newly reintroduced Dengue virus type 3 in Martinique (Peyrefitte et al., 2003; SEQ ID No.8). A dengue serotype 4 (DEN-4) may be the wild type strain 1036.

By "live attenuated" virus or strain, we mean here strain or virus that cause mild (i.e. acceptable in terms of regulatory purposes as presenting a positive benefit/risk ratio) to low or no secondary effects (i.e. systemic events and/or biological abnormalities and/or local reactions) in the majority of the tested humans but still infect and induce an immune response. These live attenuated strains may initially derived from Dengue wild-type strains.

By "immune response", we mean here a response comprising a specific humoral immune response including neutralizing antibodies in primate especially in humans. The induction of a specific humoral immune response can be easily determined by an ELISA assay. The presence of neutralizing antibody in the serum of a vaccine is evaluated by the plaque reduction neutralization test as described in Huang et al (2000). A serum is considered to be positive for the presence of neutralizing antibodies when the neutralizing antibody titer thus determined is at least superior or equal to 1:10.

Dengue strains which can be used as a starting product for the construction of the chimeric dengue virus of the invention are e.g.:

the "LAV1" strain, which is the attenuated strain established after 13 passages of Dengue serotype 1 (DEN-1) strain 16007 in Primary Dog Kidney (PDK). LAV1 sequence is shown in SEQ ID No.9. As compared with DEN-1 16007, LAV1 bears 14 nucleotide substitutions: 1323 T>C, 1541 G>A, 1543 A>G, 1545 G>A, 1567 A>G, 1608 C>T, 2363 A>G, 2695 T>C, 2782 C>T, 5063 G>A, 6048 A>T, 6806 A>G, 7330 A>G, and 9445 C>T. The above-mentioned LAV 1 strain has been described in EP 1159968 in the name of the Mahidol University and was deposited before the Collection Nationale de Culture de Microorganismes (CNCM) on May 25, 2000, under number I-2480.

the "LAV2" strain, which is the attenuated strain established after 53 passages of Dengue serotype 2 (DEN-2) strain 16681 in PDK cells. LAV2 nucleotide sequence is shown in SEQ ID No.10. As compared with the genome sequence of strain 16681, LAV2 bears 9 nucleotide substitutions: 57 C>T, 524 A>T, 2055 C>T, 2579 G>A, 4018 C>T, 5270 A>(A/T), 5547 T>C, 6599 G>C, and 8571 C>T. The above-mentioned LAV2 strain has been described in EP 1159968 in the name of the Mahidol University and was deposited before the CNCM on May 25, 2000, under number I-2481.

the "LAV3" strain, which corresponds to a strain which has been established after 30 passages of Dengue serotype 3 (DEN-3) strain 16562 in Primary Green Monkey Kidney (PGMK) cells and 3 passages in Fetal Rhesus Lung (FRhL) cells. LAV3 nucleotide sequence is shown in SEQ ID No.11. The above-mentioned LAV3 strain has been described in EP 1159968 in the name of the Mahidol University and was deposited before the CNCM on May 25, 2000, under number I-2482.

the "LAV4" strain, which corresponds to a strain which has been established after 18 passages of Dengue serotype 4 (DEN-4) strain 1036 in Primary Dog Kidney (PDK) cells. LAV4 nucleotide sequence is shown in SEQ ID No.12 The above-mentioned LAV4 strain has been described in EP 1159968 in the name of the Mahidol University and was deposited before the CNCM on May 25, 2000, under number 1-2483.

Live attenuated Vero-Derived serotype 1 and 2 viruses (VDV1 and VDV2) can also advantageously be used as the starting Dengue strain to construct the chimeric dengue viruses of the invention. VDV1 and VDV2 have been developed by the Applicant through a complex isolation and transfection process comprising various steps including in particular transfecting Vero cells with the purified genomic RNA of respectively LAV1 and LAV2 and plaque purifications. As compared with the genome sequence of strain LAV1, VDV1 (SEQ ID No.13) bears three nucleotide substitutions: 5962 C>A, and 7947 A>G, and optionally 2719 G>A. As compared with the genome sequence of strain LAV2, VDV2 (SEQ ID No.14) bears the following nucleotide substitutions: 736 G>C, 1619 G>A, 4723 T>A, 5062 G>C, 9191 G>A, 10063 T>A, and 10507 A>G, and optionally 1638 A>G, 2520 G>A, and 9222 A>G.

Substitutions identified in Dengue virus genomic sequences or polyproteins are designated pursuant to the nomenclature of Dunnen and Antonarakis (2000). As defined by Dunnen and Antonarakis at the nucleic acid level, substitutions are designated by ">", e.g. "31A>G" denotes that, at nucleotide 31 of the reference sequence, a A is changed to a G.

Chimeric Dengue/Yellow Fever Viruses

The invention thus provides an isolated live chimeric Dengue virus, advantageously an isolated live attenuated chimeric dengue virus, in which the non structural sequence NS5 of the Dengue virus is replaced by the corresponding NS5 sequence of a Yellow Fever virus. Advantageously, the 3'NCR sequence of the Dengue virus is also replaced by the corresponding 3'NCR sequence of the same Yellow Fever virus.

This chimeric Dengue strain can be constructed and isolated using, for example, the protocol described in the attached examples.

These live chimeric dengue strains can be constructed starting from an attenuated dengue strain or from wild type dengue strain. In this latter case, the chimeric virus can then be attenuated, e.g. by serial passage on cell culture such as VERO cells.

Accordingly, in one embodiment, the chimeric dengue virus of the invention is constructed starting from a live attenuated Dengue strain. In a specific embodiment, said one Dengue strain is selected from the group consisting of LAV1 (SEQ ID No.9), LAV2 (SEQ ID No.10), LAV3 (SEQ ID No.11), LAV4 (SEQ ID No.12), Vero-Derived serotype 1 (SEQ ID No.13), and Vero-Derived serotype 2 (SEQ ID No.14).

In a particular embodiment, the NS5 sequence and optionally 3'-NCR sequence incorporated in these above listed attenuated strains are from the Yellow Fever vaccinal strain YF17D (SEQ ID No.7)

The thus produced chimeric dengue viruses can be stored either in the form of a freezed composition or in the form of a lyophilized product. For that purpose, the chimeric dengue virus is mixed with a diluent such as a buffered aqueous solution comprising cryoprotective compounds such sugar alcohol and stabilizer. The pH before freezing or lyophilisation is advantageously settled in the range of 6 to 9, e.g. 7, as determined by a pH meter at room temperature. Before use, the lyophilized product is mixed with a pharmaceutically acceptable diluent or excipient such as a sterile NaCl 4% solution to reconstitute a liquid immunogenic composition or vaccine.

Sequencing at the attenuation-specific loci of the virus recovered after transfection or after serial passages (e.g. 10 passages) on cell cultures allow to confirm the high genetic stability of the chimeric constructs.

Nucleic Acid

The invention also relates to an isolated nucleic acid encoding a chimeric Dengue virus of the invention as defined above. The said nucleic acid thus comprises, or consists of, the 5'-noncoding region (NCR), structural sequences (capsid (C), premembrane/membrane (prM/M), and envelope (E)) and non structural sequences NS1, NS2A, NS2B, NS3, NS4A, and NS4B of one Dengue strain, and the non structural sequence NS5 of a Yellow fever virus and either the 3'-NCR sequence of said Dengue strain or advantageously the 3'-NCR sequence of said Yellow Fever virus.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

The present invention thus provides a cDNA sequence encoding a chimeric Dengue virus of the invention, as well as its equivalent RNA sequence.

By "equivalent RNA sequence" is meant the said DNA sequence wherein deoxythymidines have been replaced by uridines.

The present invention thus also provides the positive strand RNA of the chimeric dengue viruses of the invention.

The invention further relates to the polyprotein encoded by the nucleic acid of the invention.

Immunogenic and Vaccine Compositions

The invention also relates to an immunogenic composition, suitable to be used as a vaccine, which comprises at least one chimeric Dengue virus according to the invention in a pharmaceutically acceptable carrier.

The immunogenic compositions according to the invention elicit a specific humoral immune response toward the dengue virus, including neutralizing antibodies.

According to one embodiment, the immunogenic composition is a vaccine.

According to an embodiment, the immunogenic is a monovalent composition, i.e. a composition which elicits a specific immune response and/or confers protection against the serotype of one Dengue serotype only.

According to another embodiment, the invention relates to a multivalent dengue immunogenic composition, i.e. a composition which elicits a specific immune response against at least 2, such as 3 or 4 dengue serotypes. Such a multivalent immunogenic composition or vaccine may be obtained by combining individual monovalent dengue vaccines. The active component of a multivalent composition of the invention which induces a specific immune response against a second serotype may be a second chimeric Dengue virus of another serotype or a live attenuated Dengue virus of another serotype. For instance, the immunogenic or vaccine multivalent composition of the invention may comprise a chimeric Dengue serotype 1 virus of the invention in combination with at least a chimeric Dengue virus or a live attenuated Dengue virus selected from the group consisting of serotype 2, serotype 3, and serotype 4.

Advantageously, the immunogenic or vaccine composition may be a tetravalent Dengue vaccine composition.

The immunogenic compositions or vaccines according to the present invention may be prepared using any conventional method known to those skilled in the art. Conventionally the antigens according to the invention are mixed with a pharmaceutically acceptable diluent or excipient, such as water or phosphate buffered saline solution, wetting agents, fillers, emulsifier and stabilizer. The excipient or diluent will be selected as a function of the pharmaceutical form chosen, of the method and route of administration and also of pharmaceutical practice. Suitable excipients or diluents and also the requirements in terms of pharmaceutical formulation, are described in Remington's Pharmaceutical Sciences, which represents a reference book in this field.

Advantageously, the immunogenic composition or vaccine corresponds to an injectable composition comprising an aqueous buffered solution to maintain e.g. a pH (as determined at RT with a pH meter) in the range of 6 to 9.

The composition according to the invention may further comprise an adjuvant, i.e. a substance which improves, or enhances, the immune response elicited by the chimeric dengue virus(es). Any pharmaceutically acceptable adjuvant or mixture of adjuvants conventionally used in the field of human vaccines may be used for this purpose.

The immunogenic compositions or vaccines according to the invention may be administered by any conventional route usually used in the field of human vaccines, such as the parenteral (e.g. intradermal, subcutaneous, intramuscular) route In the context of the present invention immunogenic compositions or vaccines are preferably injectable compositions administered subcutaneously in the deltoid region.

Method for Immunizing

The invention further provides for a method of immunizing a host in need thereof against a Dengue infection which comprises administering the host with an immunoeffective amount of an immunogenic composition or a vaccine according to the invention.

A "host in need thereof" denotes a person at risk for Dengue infection, i.e. individuals travelling to regions where Dengue virus infection is present, and also inhabitants of those regions.

The route of administration is any conventional route used in the vaccine field. The choice of administration route depends on the formulation that is selected. Preferably, the immunogenic composition or vaccine corresponds to an injectable composition administered via subcutaneous route, advantageously in the deltoid region.

The amount of live attenuated chimeric Dengue virus in the immunogenic compositions or vaccines may be conveniently expressed in viral plaque forming unit (PFU) unit or Cell Culture Infectious Dose 50% ($CCID_{50}$) dosage form and prepared by using conventional pharmaceutical techniques. For instance, the composition according to the invention may be prepared in dosage form containing 10 to $10^6$ $CCID_{50}$, or from $10^3$ to $10^5$ $CCID_{50}$ of virus, for instance $4\pm0.5$ $\log_{10}$ $CCID_{50}$ of live attenuated chimeric Dengue virus for a monovalent composition. Where the composition is multivalent, to reduce the possibility of viral interference and thus to achieve a balanced immune response (i.e. an immune response against all the serotype contained in the composition), the amounts of each of the different dengue serotypes present in the administered vaccines may not be equal.

An "immunoeffective amount" is an amount which is capable of inducing a specific humoral immune response comprising neutralising antibodies in the serum of a vaccine. Methods for evaluating the presence of neutralizing antibodies are well known by the one skilled in the art.

The volume of administration may vary depending on the route of administration. Subcutaneous injections may range in volume from about 0.1 ml to 1.0 ml, preferably 0.5 ml.

The optimal time for administration of the composition is about one to three months before the initial exposure to the dengue virus. The vaccines of the invention can be administered as prophylactic agents in adults or children at risk of Dengue infection. The targeted population thus encompasses persons which are naïve as well as well as non-naïve with regards to dengue virus. The vaccines of the invention can be administered in a single dose or, optionally, administration can involve the use of a priming dose followed by a booster dose that is administered, e.g. 2-6 months later, as determined to be appropriate by those of skill in the art.

The invention will be further described in view of the following figures and examples. For sake of clarity the following description details only the construction of a chimeric dengue virus of the invention from a LAV3 backbone.

EXAMPLES

Example 1

Construction of a Chimeric Dengue 3 Virus Containing the Yellow Fever NS5 Sequence To construct a chimeric dengue 3 virus of the invention, The complete Dengue 3 genomic cDNA (SEQ ID No.11) can be cloned into a vector pVAX (Invitrogen) containing the T7 RNA polymerase promoter and engineered such that the unique NotI restriction site is flanking the 3' end of the viral sequence.

To link Dengue 3 NS4b and Yellow Fever NS5 one can use the following strategy based on the technique of overlap extension. This technique is advantageously selected for it's capacity to perfectly fuse two genetic sequence avoiding the need to create new restriction sites at the point of junction.

The Dengue—Yellow Fever chimeric construct can be generated using three consecutive PCR steps, as shown on the diagrammatic representation on FIG. 1 and as described below.

Figure 3:
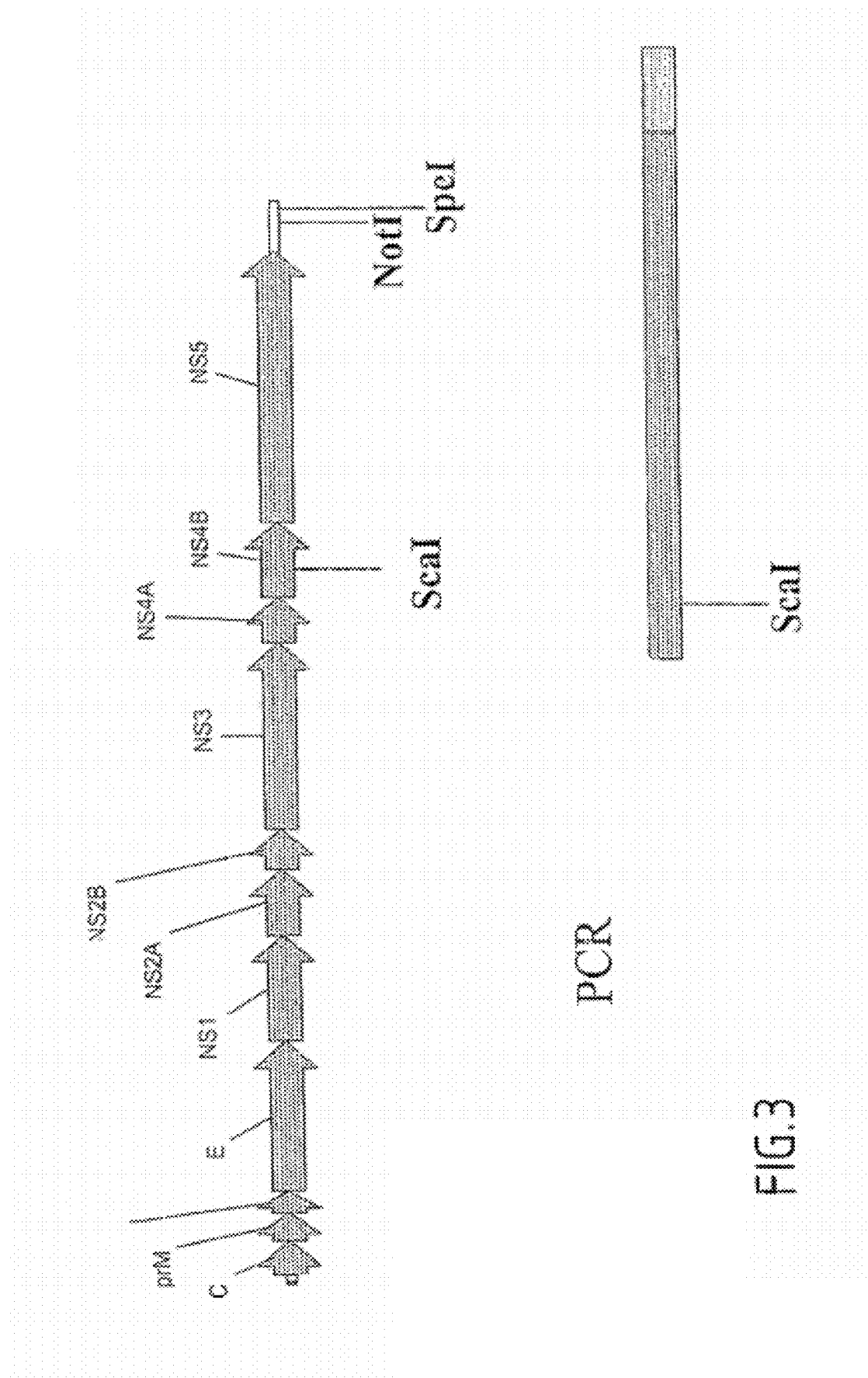
FIG. 3 shows the position of the ScaI restriction sites on Dengue-3 genome and on the amplicon PCR1.

In the first PCR step, two partially overlapping DNA fragments (PCR1 and PCR2) are generated as follows:

The PCR1 fragment is generated according to the strategy displayed on FIG. 3.

| PCR 1 | |
|---|---|
| Plasmid DNA (50 ng/µl) | 0.5 µl |
| 10x Buffer | 5 µl |
| Primer 1 (125 ng/µl) | 1 µl |
| Primer 2 (125 ng/µl) | 1 µl |
| dNTP 1.25 mM | 8 µl |
| Nuclease-free water | 34.5 µl |
| Final volume | 50 µl |

+1 µl de Platinum Hi Fi Taq polymerase with

```
Primer-1:
                                    (SEQ ID No. 1)
CGGCAGTACTTTTGCTAATCACACATTATG Primer-2:
                                    (SEQ ID No. 2)
TTTTTCCATTCGCGCTCCCTCTTTTTCCTGTTCCAACTG
```

Primer 1 is located into the NS4b of Dengue 3 (nucleotides 7146 to 7175 of Dengue 3 sequence SEQ ID No.9) and contains the unique ScaI restriction site (underlined). Primer 2 overlaps NS4b Dengue 3 (bold characters) and NS5 Yellow Fever sequences.

Program:

| Initial denaturation | 95° C. | 30 sec | |
|---|---|---|---|
| Denaturation | 95° C. | 30 sec | |
| Hybridization | 57° C. | 1 min | for 30 cycles |
| Elongation | 68° C. | 1 min | |

A 0.45 Kb fragment containing about 430 nucleotides of the Dengue NS4b sequence and a small extension corresponding to the 5' end of the Yellow Fever NS5 sequence can thus be obtained (PCR1, SEQ ID No.3).

Figure 4:
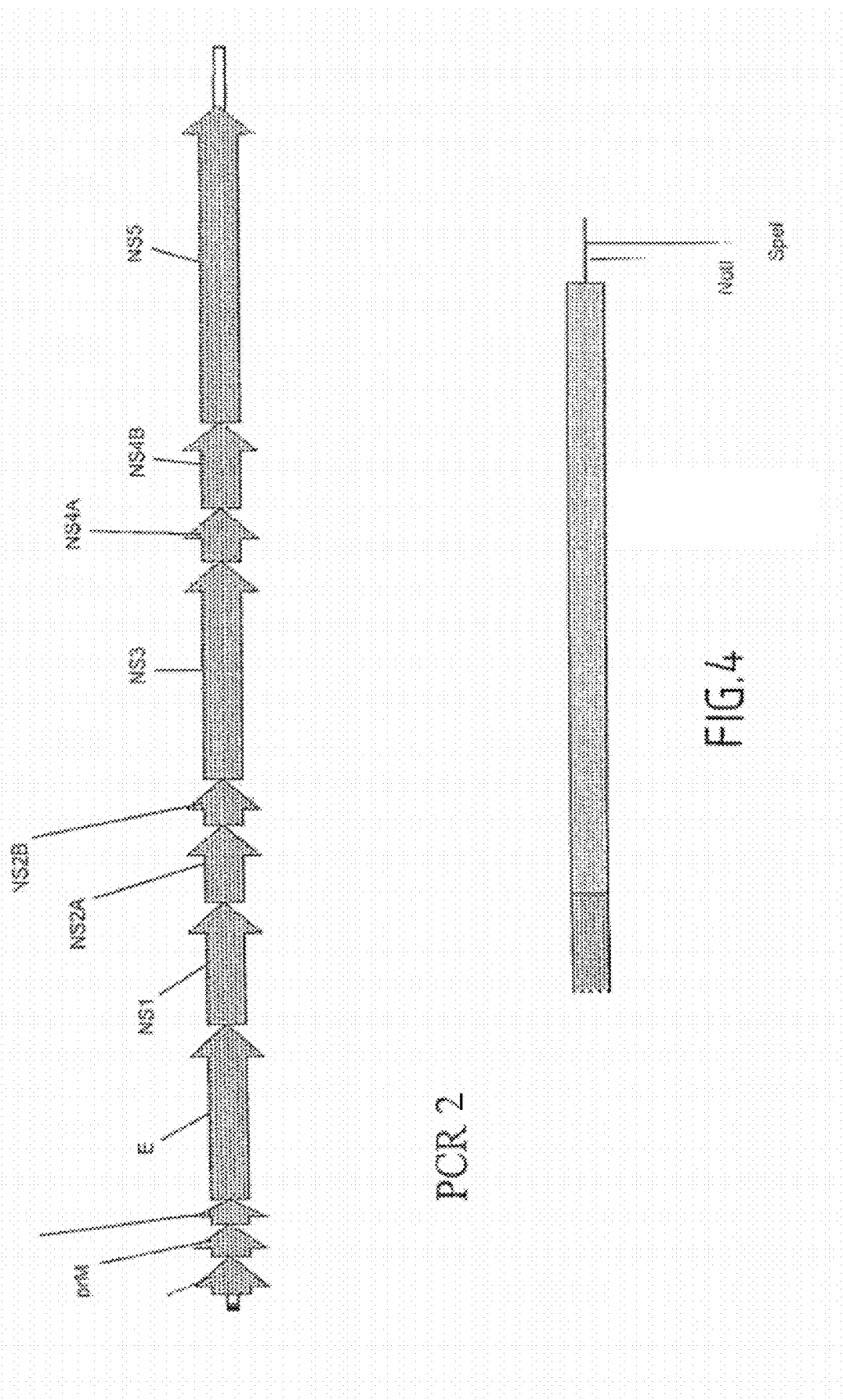
FIG. 4 shows the position of the NotI and SpeI restriction sites on Dengue-3 genome and on the amplicon PCR2.

The PCR2 fragment is generated according to the strategy displayed on FIG. 4.

| PCR 2 | |
|---|---|
| cDNA from YF virus (50 ng/µl) | 0.5 µl |
| 10x Buffer | 5 µl |
| Primer 3 (125 ng/µl) | 1 µl |

-continued

PCR 2

| | |
|---|---|
| Primer 4 (125 ng/µl) | 1 µl |
| dNTP 1.25 mM | 8 µl |
| Nuclease-free water | 34.5 µl |
| Final volume | 50 µl |

+1 µl de Platinum Hi Fi Taq polymerase with

```
                                                     (SEQ ID No. 4)
Primer-3    CAGTTGGAACAGGAAAAAGAGGGAGCGCGAATGGAAAAA (SEQ ID No. 5)
Primer-4    GGACTAGTAACGCCGGCGAGTGGTTTTGTGTTTGTCATC
```

Primer 3 overlaps NS4b Dengue 3 and NS5 Yellow Fever (bold characters) and is the reverse complement of primer 2. Primer 4 is located into the 3'UTR of Yellow Fever and contains Not I and Spe I restriction sites (underlined)

Program:

| | | | |
|---|---|---|---|
| Initial denaturation | 95° C. | 30 sec | |
| Denaturation | 95° C. | 30 sec | |
| Hybridization | 57° C. | 1 min | 30 cycles |
| Elongation | 68° C. | 4 min | |

A 3.2 Kb fragment containing 15 Nucleotides of the 5' end of the Dengue NS4b sequence and the complete sequence encoding the Yellow Fever NS5 encoding sequence and the 3' region non coding sequence of the Yellow Fever genome can thus be obtained (PCR2, SEQ ID No.6).

Figure 5:
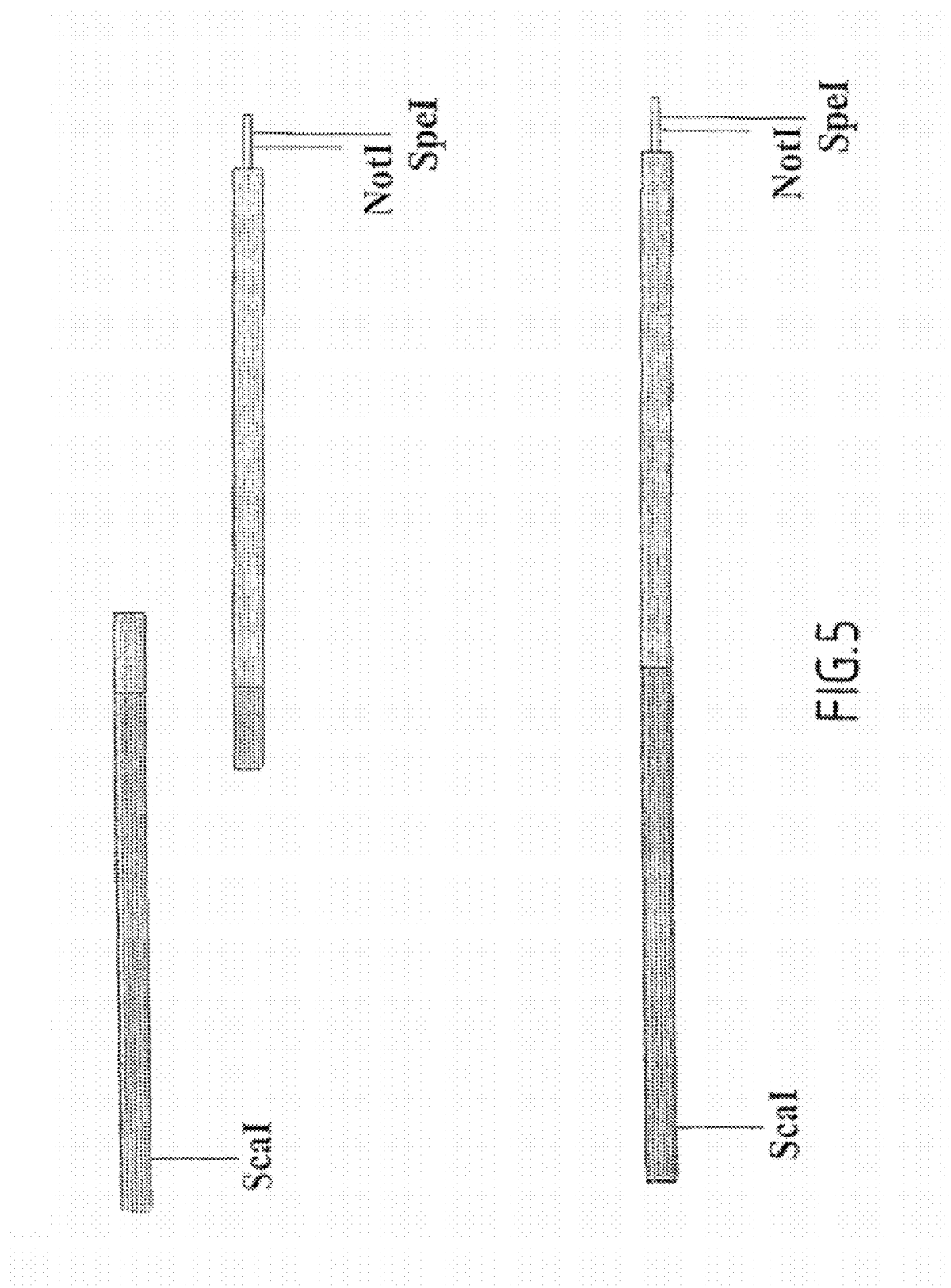
FIG. 5 shows overlapping between amplicons PCR1 and PCR2.

In a second PCR step (reaction PCR3, FIG. 5), a stoechiometric mixture of both partially overlapping fragments PCR1 and PCR2 is submitted to 10 PCR cycles. No primer is added.

PCR 3

| | |
|---|---|
| Product of PCR 1 | 0.5 µl |
| Product of PCR 2 | 0.5 µl |
| 10x Buffer | 5 µl |
| dNTP 1.25 mM | 8 µl |
| Nuclease-free water | 36 µl |
| Final volume | 50 µl |

+1 µl de Platinum Hi Fi Taq polymerase

Program:

| | | | |
|---|---|---|---|
| Initial denaturation | 95° C. | 30 sec | |
| Denaturation | 95° C. | 30 sec | |
| Hybridisation | 57° C. | 1 min | 10 cycles |
| Elongation | 68° C. | 4 min | |

The third PCR step (reaction PCR4) is carried out with the product of the second reaction in the presence of primers 1 and 4 containing respectively the ScaI and Not/Spe restriction sites. To that end 1 µl of each of primer 1 and primer 4 (125 ng/µl) is added to the reaction product of PCR3 and the PCR reaction is continued for 25 additional cycles.

The resulting large DNA fragment can be purified on agarose gel, then digested with ScaI and NotI or SpeI restriction endonucleases and ligated to the original vector containing the whole Dengue 3 sequence.

Example 2

Recovery of Chimeric Dengue Viruses

To recover the chimeric dengue viruses, the following strategy can be used.

All recombinant plasmids can be amplified in *Escherichia coli* XL1-Blue cells. 500 ng of plasmid are then linearized by the NotI restriction endonuclease. Viral RNA can be obtained after in vitro transcription using T7 RNA polymerase and capped with the cap analog $m^7$ GpppA. And, then transfected into $3 \times 10^6$ to $4 \times 10^6$ LLC-$MK_2$ or BHK-21 cells by electroporation. Transfected cells are transferred to 75-$cm^2$ flasks in DMEM containing 10% FBS. The resulting chimeric virus is then amplified and isolated from the cells.

REFERENCES

Dunnen and Antonarakis (2000) Mutation nomenclature extensions and suggestions to describe complex mutations: a discussion. Hum Mutation. 15:7-12; Erratum in: Hum Mutat 2002; 20(5):403

Freestone, in Plotkin et al., eds, Vaccines, $2^{nd}$ ed, W. B, Saunders, PA, 1995

Gubler D J. Dengue. (1988) In: Epidemiology of arthropod-borne viral disease. Monath T P M, editor, Boca Raton (FL): CRC Press:223-60

Gubler D J, Kuno G. Dengue and Dengue Hemorrhagic Fever. CAB International Publishing 1997

Huang et al. (2000), J. Virol. 74; 3020-3028

Kautner I, Robinson M J, Kubnle U. (1997) Dengue Virus infection: Epidemiology, pathogenesis, clinical presentation, diagnosis, and prevention. J of Pediatrics; 131:516-524

Peyrefitte, C. N., Couissinier-Paris, P., Mercier-Perennec, V., Bessaud, M., Martial, J., Kenane, N., Durand, J. P. and Tolou, H. J. (2003) Genetic Characterization of Newly Reintroduced Dengue Virus Type 3 in Martinique (French West Indies). J. Clin. Microbiol. 41 (11), 5195-5198

Pugachev K V et al., (2004) High Fidelity of Yellow Fever Virus RNA Polymerase. Journal of Virology, 78, p. 1032-1038

Rice, C. M., Lenches, E. M., Eddy, S. R., Shin, S. J., Sheets, R. L. and Strauss, J. H. (1985) Nucleotide sequence of yellow fever virus: implications for flavivirus gene expression and evolution. Science; 229, 726-733

Rigau-Pérez J G, Clark G G, Gubler D J, Reiter P, Sanders E J, Vorndam A V. (1998) Dengue and dengue haemorrhagic fever. Lancet; 352: 971-977.

Rothman A L, Ennis F A. (1999) Immunopathogenesis of dengue haemorrhagic fever. Virology; 257: 1-6

Sabin A B. (1952) Research on dengue during World War II. Am J Trop Med Hyg; 1: 30-50

Smithburn et al., (1956) Yellow Fever Vaccination, World Health Org. p. 238

Vaughn D W, Green S, Kalayanarooj S, Innis B L, Nimmannitya S, Suntayakorn S, Rothman A L, Ennis F A, Nisalak A. (1997) Dengue in the early febrile phase: viremia and antibody response. J Infect Dis; 176: 322-30

Vaughn D W, Green S, Kalayanarooj S, Innis B L, Nimmannitya S, Suntayakorn S, Endy T P, Raengsakulrach B, Rothman A L, Ennis F A, Nisalak A. (2000) Dengue viremia titer, antibody response pattern, and virus serotype correlate with disease severity. J Inf Dis; 181: 2-9

WHO Technical Guide, (1986) Dengue haemorrhagic fever: diagnosis, treatment and control, p 1-2. World Health Organization, Geneva, Switzerland Wu S, Grouard-Vogel G, Sun W, Mascola J, Brachtel E, Putvatana R. (2000) Human skin Langerhans cells are targets of dengue virus infection. Nature Med; 7:816-820

I claim

1. An isolated nucleic acid encoding a live attenuated chimeric Dengue virus, comprising:
   (a) the 5'-noncoding region (NCR), structural sequences capsid, premembrane/membrane, and envelope, and non-structural sequences NS1, NS2A, NS2B, NS3, NS4A, and NS4B of a Dengue viral strain;
   (b) the non-structural sequence NS5 of a Yellow Fever viral strain; and
   (c) the 3'-NCR sequence of the Dengue viral strain or the Yellow Fever viral strain.

2. The isolated nucleic acid of claim 1, wherein the Dengue viral strain is from Dengue serotype 1, Dengue serotype 2, Dengue serotype 3, or Dengue serotype 4 viruses.

3. The isolated nucleic acid of claim 1, wherein the Dengue viral strain is LAV1 (SEQ ID NO: 9).

4. The isolated nucleic acid of claim 1, wherein the Yellow Fever viral strain is YF17D (SEQ ID NO: 7).

5. A vector comprising the isolated nucleic acid molecule of claim 1.

6. An isolated host cell comprising the nucleic acid molecule of claim 1.

7. An isolated host cell comprising the vector of claim 5.

8. A process of producing a polypeptide encoded by the nucleic acid molecule of claim 1 comprising culturing an isolated host cell comprising the nucleic acid molecule of claim 1 under suitable conditions to express the polypeptide, and optionally isolating the polypeptide.

9. A process of producing a polypeptide encoded by the vector of claim 5 comprising culturing an isolated host cell comprising the vector of claim 5 under suitable conditions to express the polypeptide, and optionally isolating the polypeptide.

* * * * *

SEQUENCE LISTING

<160> NUMBER OF SEQ ID NOS: 14

<210> SEQ ID NO 1
<211> LENGTH: 30
<212> TYPE: DNA
<213> ORGANISM: Artificial
<220> FEATURE:
<223> OTHER INFORMATION: Synthetic, PCR primer for NS4b of Dengue 3

<400> SEQUENCE: 1
cggcagtact tttgctaatc acacattatg                30

<210> SEQ ID NO 2
<211> LENGTH: 39
<212> TYPE: DNA
<213> ORGANISM: Artificial
<220> FEATURE:
<223> OTHER INFORMATION: Synthetic, PCR primer for NS4b of Dengue 3 and
      NS5 of Yellow Fever Virus

<400> SEQUENCE: 2
tttttccatt cgcgctccct cttttccctg ttccaactg                39

<210> SEQ ID NO 3
<211> LENGTH: 438
<212> TYPE: DNA
<213> ORGANISM: Artificial
<220> FEATURE:
<223> OTHER INFORMATION: Synthetic, product of PCR reaction

<400> SEQUENCE: 3
cggcagtact cttgctgatc acacattatg ctattatagg tccaggattg caggcaaaag     60
ccactcgtga agctcagaaa aggacagctg ctggaataat gaagaatcca acggtggatg    120
ggataatgac aatagaccta gatcctgtaa tatatgattc aaaatttgaa aagcaactgg    180
gacaggttat gctcctggtt ttgtgtgcag ttcaactttt gttaatgaga acatcatggg    240
ccttgtgtga agctttaact ctagctacag gaccaataac aacactctgg gaaggatcac    300
ctgggaagtt tggaacacc acgatagctg tttccatggc gaacattttt agagggagct    360
atttagcagg agctgggctt gcttttttcta ttatgaaatc agttggaaca ggaaaaagag    420
ggagcgcgaa tggaaaaa                                                  438

<210> SEQ ID NO 4
<211> LENGTH: 39
<212> TYPE: DNA
<213> ORGANISM: Artificial
<220> FEATURE:
<223> OTHER INFORMATION: Synthetic, PCR primer for NS4b Dengue 3 and NS5
      Yellow Fever

<400> SEQUENCE: 4
cagttggaac aggaaaaaga gggagcgcga atggaaaaa                39

<210> SEQ ID NO 5
<211> LENGTH: 39
<212> TYPE: DNA
<213> ORGANISM: Artificial
<220> FEATURE:
<223> OTHER INFORMATION: Synthetic, PCR primer for 3' UTR of Yellow Fever virus

<400> SEQUENCE: 5
ggactagtaa cgccggcgag tggttttgtg tttgtcatc                         39

<210> SEQ ID NO 6
<211> LENGTH: 3246
<212> TYPE: DNA
<213> ORGANISM: Artificial
<220> FEATURE:
<223> OTHER INFORMATION: Synthetic, product of PCR reaction

<400> SEQUENCE: 6
cagttggaac aggaaaaaga gggagcgcga atggaaaaac tttgggtgaa gtctggaaga    60
gggaactgaa tctgttggac aagcgacagt ttgagttgta taaaaggacc gacattgtgg   120
aggtggatcg tgatacggca cgcaggcatt tggccgaagg aaggtggac accggggtgg    180
cggtctccag ggggaccgca aagttaaggt ggttccatga gcgtggctat gtcaagctgg   240
aaggtagggt gattgacctg gggtgtggcc gcggaggctg tgttactac gctgctgcgc    300
aaaaggaagt gagtggggtc aaaggattta ctcttggaag agacggccat gagaaaccca   360
tgaatgtgca aagtctggga tggaacatca tcaccttcaa ggacaaaact gatatccacc   420
gcctagaacc agtgaaatgt gacacccttt tgtgtgacat tggagagtca tcatcgtcat   480
cggtcacaga gggggaaagg accgtgagag ttcttgatac tgtagaaaaa tggctggctt   540
gtggggttga caacttctgt gtgaaggtgt tagctccata catgccagat gttctcgaga   600
aactggaatt gctccaaagg aggtttggcg aacagtgat caggaaccct ctctccagga   660
attccactca tgaaatgtac tacgtgtctg gagcccgcag caatgtcaca tttactgtga   720
accaaacatc ccgcctcctg atgaggagaa tgaggcgtcc aactggaaaa gtgaccctgg   780
aggctgacgt catcctccca attgggacac gcagtgttga gacagacaag gaccccctgg   840
acaaagaggc catagaagaa agggttgaga ggataaaatc tgagtacatg acctcttggt   900
tttatgacaa tgacaacccc tacaggacct ggcactactg ggctcctat gtcacaaaaa    960
cctcaggaag tgcggcgagc atggtaaatg gtgttattaa aattctgaca tatccatggg   1020
acaggataga ggaggtcaca agaatggcaa tgactgacac aacccctttt ggacagcaaa   1080
gagtgtttaa agaaaaagtt gacaccagag caaaggatcc accagcggga actaggaaga   1140
tcatgaaagt tgtcaacagg tggctgttcc gccacctggc cagagaaaag aaccccagac   1200
tgtgcacaaa ggaagaattt attgcaaaag tccgaagtca tgcagccatt ggagcttacc   1260
tggaagaaca agaacagtgg aagactgcca atgaggctgt ccaagaccca agttctgggg   1320
aactggtgga tgaagaaagg aagctgcacc aacaaggcag gtgtcggact tgtgtgtaca   1380
acatgatggg gaaagagag aagaagctgt cagagtttgg gaaagcaaag ggaagccgtg   1440
ccatatggta tatgtggctg ggagcgcggt atcttgagtt tgaggccctg ggattcctga   1500
atgaggacca ttgggcttcc agggaaaact caggaggagg agtggaaggc attggcttac   1560
aataccctagg atatgtgatc agagacctgg ctgcaatgga tggtggtgga ttctacgcgg   1620
atgacaccgc tggatgggac acgcgcatca cagaggcaga ccttgatgat gaacaggaga   1680
tcttgaacta catgagccca catcacaaaa aactggcaca agcagtgatg gaaatgacat   1740
acaagaacaa agtggtgaaa gtgttgagac agcccccagg agggaaagcc tacatggatg   1800
tcataagtcg acgagaccag agaggatccg ggcaggtagt gacttatgct ctgaacacca   1860
tcaccaactt gaaagtccaa ttgatcagaa tggcagaagc agagatggtg atacatcacc   1920

```
aacatgttca agattgtgat gaatcagttc tgaccaggct ggaggcatgg ctcactgagc   1980
acggatgtga cagactgaag aggatggcgg tgagtggaga cgactgtgtg gtccggccca   2040
tcgatgacag gttcggcctg cccctgtccc atctcaacgc catgtccaag gttagaaagg   2100
acatatctga tggcagcca tcaaaagggt ggaatgattg ggagaatgtg cccttctgtt    2160
cccaccactt ccatgaacta cagctgaagg atggcaggag gattgtggtg ccttgccgag   2220
aacaggacga gctcattggg agaggaaggg tgtctccagg aaacggctgg atgatcaagg   2280
aaacagcttg cctcagcaaa gcctatgcca acatgtggtc actgatgtat tttcacaaaa   2340
gggacatgag gctactgtca ttggctgttt cctcagctgt tcccacctca tgggttccac   2400
aaggacgcac aacatggtcg attcatggga aggggagtg gatgaccacg aagacatgc     2460 ttgaggtgtg aacagagta tggataacca acaacccaca catgcaggac aagacaatgg    2520
tgaaaaaatg gagagatgtc ccttatctaa ccaagagaca agacaagctg tgcggatcac   2580
tgattggaat gaccaatagg gccacctggg cctcccacat ccatttagtc atccatcgta   2640
tccgaacgct gattggacag gagaaataca ctgactacct aacagtcatg gacaggtatt   2700
ctgtggatgc tgacctgcaa ctgggtgagc ttatctgaaa caccatctaa caggaataac   2760
cgggatacaa accacgggtg gagaaccgga ctccccacaa cctgaaaccg ggatataaac   2820
cacggctgga gaaccgggct ccgcacttaa aatgaaacag aaaccgggat aaaaactacg   2880
gatggagaac cggactccac acattgagac agaagaagtt gtcagcccag aacccacac    2940 gagttttgcc actgctaagc tgtgaggcag tgcaggctgg gacagccgac tccaggttg    3000 cgaaaaacct ggtttctggg acctcccacc ccagagtaaa agaacggag cctccgctac    3060 caccctccca cgtggtggta gaaagacggg gtctagaggt tagaggagac cctccaggga   3120
acaaatagtg ggaccatatt gacgccaggg aaagaccgga gtggttctct gcttttcctc   3180
cagaggtctg tgagcacagt ttgctcaaga ataagcagac cttggatga caaacacaaa    3240 accact                                                              3246

<210> SEQ ID NO 7
<211> LENGTH: 10862
<212> TYPE: DNA
<213> ORGANISM: Yellow fever virus

<400> SEQUENCE: 7
agtaaatcct gtgtgctaat tgaggtgcat tggtctgcaa atcgagttgc taggcaataa    60
acacatttgg attaatttta atcgttcgtt gagcgattag cagagaactg accagaacat   120
gtctggtcgt aaagctcagg gaaaaaccct gggcgtcaat atggtacgac gaggagttcg   180
ctccttgtca aacaaaataa aacaaaaaac aaaacaaatt ggaaacagac tggaccttc    240 aagaggtgtt caaggattta tcttttttctt tttgttcaac attttgactg gaaaaaagat   300
cacagcccac ctaaagaggt tgtggaaaat gctggaccca agacaaggct tggctgttct   360
aaggaaagtc aagagagtgg tggccagttt gatgagagga ttgtcctcaa ggaaacgccg   420
ttcccatgat gttctgactg tgcaattcct aattttggga atgctgttga tgacgggtgg   480
agtgaccttg gtgcggaaaa acagatggtt gctcctaaat gtgacatctg aggacctcgg   540 gaaacattc tctgtgggca caggcaactg cacaacaaac attttggaag ccaagtactg    600
gtgcccagac tcaatggaat acaactgtcc caatctcagt ccaagagagg agccagatga   660
cattgattgc tggtgctatg ggtggaaaa cgttagagtc gcatatggta agtgtgactc    720
agcaggcagg tctaggaggt caagaagggc cattgacttg cctacgcatg aaaaccatgg   780
```

-continued

```
tttgaagacc cggcaagaaa aatggatgac tggaagaatg ggtgaaaggc aactccaaaa    840
gattgagaga tggttcgtga ggaaccccct ttttgcagtg acggctctga ccattgccta    900
ccttgtggga agcaacatga cgcaacgagt cgtgattgcc ctactggtct tggctgttgg    960
tccggcctac tcagctcact gcattggaat tactgacagg gatttcattg agggggtgca   1020
tggaggaact tgggtttcag ctaccctgga gcaagacaag tgtgtcactg ttatggcccc   1080
tgacaagcct tcattggaca tctcactaga gacagtagcc attgatagac ctgctgaggt   1140
gaggaaagtg tgttacaatg cagttctcac tcatgtgaag attaatgaca agtgccccag   1200
cactggagag gcccacctag ctgaagagaa cgaaggggac aatgcgtgca agcgcactta   1260
ttctgataga ggctggggca atggctgtgg cctatttggg aaagggagca ttgtggcatg   1320
cgccaaattc acttgtgcca aatccatgag tttgtttgag gttgatcaga ccaaaattca   1380
gtatgtcatc agagcacaat tgcatgtagg ggccaagcag gaaaattgga ataccgacat   1440
taagactctc aagtttgatg ccctgtcagg ctcccaggaa gtcgagttca ttgggtatgg   1500
aaaagctaca ctggaatgcc aggtgcaaac tgcggtggac tttggtaaca gttacatcgc   1560
tgagatggaa acagagagct ggatagtgga cagacagtgg gcccaggact tgaccctgcc   1620
atggcagagt ggaagtggcg gggtgtggag agagatgcat catcttgtcg aatttgaacc   1680
tccgcatgcc gccactatca gagtactggc cctgggaaac caggaaggct ccttgaaaac   1740
agctcttact ggcgcaatga gggttacaaa ggacacaaat gacaacaacc tttacaaact   1800
acatggtgga catgtttctt gcagagtgaa attgtcagct ttgacactca aggggacatc   1860
ctacaaaata tgcactgaca aaatgttttt tgtcaagaac ccaactgaca ctggccatgg   1920
cactgttgtg atgcaggtga aagtgtcaaa aggagccccc tgcaggattc cagtgatagt   1980
agctgatgat cttacagcgg caatcaataa aggcattttg gttacagtta accccatcgc   2040
ctcaaccaat gatgatgaag tgctgattga ggtgaaccca ccttttggag acagctacat   2100
tatcgttggg agaggagatt cacgtctcac ttaccagtgg cacaaagagg gaagctcaat   2160
aggaaagttg ttcactcaga ccatgaaagg cgtggaacgc ctggccgtca tgggagacac   2220
cgcctgggat ttcagctccg ctggagggtt cttcacttcg gttgggaaag gaattcatac   2280
ggtgtttggc tctgcctttc aggggctatt tggcggcttg aactggataa caaaggtcat   2340
catgggggcg gtacttatat gggttggcat caacacaaga aacatgacaa tgtccatgag   2400
catgatcttg gtaggagtga tcatgatgtt tttgtctcta ggagttgggg cggatcaagg   2460
atgcgccatc aactttggca agagagagct caagtgcgga gatggtatct tcatatttag   2520
agactctgat gactggctga acaagtactc atactatcca gaagatcctg tgaagcttgc   2580
atcaatagta aaagcctctt ttgaagaagg gaagtgtggc ctaaattcag ttgactccct   2640
tgagcatgag atgtggagaa gcagggcaga tgagatcaat gccattttg aggaaaacga   2700
ggtggacatt tctgttgtcg tgcaggatcc aaagaatgtt taccagagag gaactcatcc   2760
attttccaga attcgggatg gtctgcagta tggttggaag acttggggta agaaccttgt   2820
gttctcccca gggaggaaga atggaagctt catcatagat ggaaagtcca ggaaagaatg   2880
cccgttttca aaccgggtct ggaattcttt ccagatagag gagtttggga cgggagtgtt   2940
caccacacgc gtgtacatgg acgcagtctt tgaatacacc atagactgcg atggatctat   3000
cttgggtgca gcggtgaacg gaaaaaagag tgcccatggc tctccaacat tttgatggg   3060
aagtcatgaa gtaaatggga catggatgat ccacaccttg gaggcattag attacaagga   3120
gtgtgagtgg ccactgacac atacgattgg aacatcagtt gaagagagtg aaatgttcat   3180
```

-continued

```
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtccctt ttggtttggt    3540
gagcatgatg atagcaatgg aagtggtcct aaggaaaaga cagggaccaa agcaaatgtt    3600
ggttggagga gtagtgctct gggagcaatg ctggtcggg caagtaactc tccttgattt     3660
gctgaaactc acagtggctg tgggattgca tttccatgag atgaacaatg gaggagacgc    3720
catgtatatg gcgttgattg ctgccttttc aatcagacca gggctgctca tcggctttgg    3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgcccct    3960
catggctctg ttgacacctg tcactatggc tgaggtgaga cttgccgcaa tgttcttttg    4020
tgccgtggtt atcataggg tccttcacca gaatttcaag gacacctcca tgcagaagac     4080
tatacctctg gtggccctca cactcacatc ttacctgggc ttgacacaac cttttttggg    4140
cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctgggag    4320
ggtggatggg ctagagctca agaagcttgg tgaagtttca tgggaagagg aggcggagat    4380
cagcgggagt tccgcccgct atgatgtggc actcagtgaa caagggagt tcaagctgct     4440
ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggt gttccacaca atgtggcatg tcacaagagg    4740
agctttcctt gtcaggaatg gcaagaagtt gattccatct tgggcttcag taaggaaga    4800
ccttgtcgcc tatggtggct catggaagtt ggaaggcaga tgggatggag aggaagaggt    4860
ccagttgatc gcggctgttc caggaaagaa cgtggtcaac gtccagacaa accgagctt     4920
gttcaaagtg aggaatgggg agaaatcgg ggctgtcgct cttgactatc cgagtggcac     4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
ggaggctttt cacggcctgg acgtgaaatt ccacacacag gcttttccg ctcacggcag     5340
cgggagagaa gtcattgatg ccatgtgcca tgccacccta acttacagga tgttggaacc    5400
aactagggtt gttaactggg aagtgatcat tatggatgaa gcccattttt tggatccagc    5460
tagcatagcc gctagaggtt gggcagcgca cagagctagg gcaaatgaaa gtgcaacaat    5520
cttgatgaca gccacaccgc ctgggactag tgatgaattt ccacattcaa atggtgaaat    5580
```

-continued

```
agaagatgtt caaacggaca tacccagtga gccctggaac acagggcatg actggatcct    5640
agctgacaaa aggcccacgg catggttcct tccatccatc agagctgcaa atgtcatggc    5700
tgcctctttg cgtaaggctg aaagagtgt ggtggtcctg aacaggaaaa cctttgagag    5760 agaataccc acgataaagc agaagaaacc tgactttata ttggccactg acatagctga    5820
aatgggagcc aacctttgcg tggagcgagt gctggattgc aggacggctt ttaagcctgt    5880
gcttgtggat gaagggagga aggtggcaat aaaagggcca cttcgtatct ccgcatcctc    5940
tgctgctcaa aggagggggc gcattgggag aaatcccaac agagatggag actcatacta    6000
ctattctgag cctacaagtg aaaataatgc ccaccacgtc tgctggttgg aggcctcaat    6060
gctcttggac aacatggagg tgaggggtgg aatggtcgcc ccactctatg gcgttgaagg    6120
aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtggtg ttttgaaggc cctgaggaac atgagatctt    6300
gaatgacagc ggtgaaacag tgaagtgcag ggctcctgga ggagcaaaga agcctctgcg    6360
cccaaggtgg tgtgatgaaa gggtgtcatc tgaccagagt gcgctgtctg aatttattaa    6420
gtttgctgaa ggtaggaggg gagctgctga agtgctagtt gtgctgagtg aactccctga    6480
tttcctggct aaaaaaggtg gagaggcaat ggataccatc agtgtgttcc tccactctga    6540
ggaaggctct agggcttacc gcaatgcact atcaatgatg cctgaggcaa tgacaatagt    6600
catgctgttt atactggctg gactactgac atcgggaatg gtcatctttt tcatgtctcc    6660
caaaggcatc agtagaatgt ctatggcgat gggcacaatg gccggctgtg atatctcat    6720 gttccttgga ggcgtcaaac ccactcacat ctcctatgtc atgctcatat tctttgtcct    6780
gatggtggtt gtgatccccg agccagggca acaaaggtcc atccaagaca accaagtggc    6840
atacctcatt attggcatcc tgacgctggt ttcagcggtg gcagccaacg agctaggcat    6900
gctggagaaa accaaagagg acctctttgg gaagaagaac ttaattccat ctagtgcttc    6960
accctggagt tggccggatc ttgacctgaa gccaggagct gcctggacag tgtacgttgg    7020
cattgttaca atgctctctc caatgttgca ccactggatc aaagtcgaat atggcaacct    7080
gtctctgtct ggaatagccc agtcagcctc agtcctttct ttcatggaca agggatacc    7140 attcatgaag atgaatatct cggtcataat gctgctggtc agtggctgga ttcaataac    7200 agtgatgcct ctgctctgtg cataggggtg cgccatgctc cactggtctc tcatttacc    7260 tggaatcaaa gcgcagcagt caaagcttgc acagagaagg gtgttccatg gcgttgccga    7320
gaaccctgtg gttgatggga atccaacagt tgacattgag gaagctcctg aaatgcctgc    7380
cctttatgag aagaaactgg ctctatatct ccttcttgct ctcagcctag cttctgttgc    7440
catgtgcaga acgcccttt cattggctga aggcattgtc ctagcatcag ctgccttagg    7500
gccgctcata gagggaaaca ccagccttct ttggaatgga cccatggctg tctccatgac    7560
aggagtcatg aggggggaatc actatgcttt tgtgggagtc atgtacaatc tatggaagat    7620
gaaaactgga cgccggggga gcgcgaatgg aaaaactttg ggtgaagtct ggaagaggga    7680
actgaatctg ttggacaagc gacagtttga gttgtataaa aggaccgaca ttgtggaggt    7740
ggatcgtgat acggcacgca ggcatttggc cgaagggaag gtggacaccg gggtggcggt    7800
ctccaggggg accgcaaagt taaggtggtt ccatgagcgt ggctatgtca agctggaagg    7860
tagggtgatt gacctggggt gtggccgcgg aggctggtgt actacgctg ctgcgcaaaa    7920 ggaagtgagt ggggtcaaag gatttactct tggaagagac ggccatgaga aacccatgaa    7980
```

```
tgtgcaaagt ctgggatgga acatcatcac cttcaaggac aaaactgata tccaccgcct   8040
agaaccagtg aaatgtgaca ccctttgtg tgacattgga gagtcatcat cgtcatcggt    8100
cacagagggg gaaaggaccg tgagagttct tgatactgta gaaaatggc tggcttgtgg    8160 ggttgacaac ttctgtgtga aggtgttagc tccatacatg ccagatgttc tcgagaaact   8220
ggaattgctc caaaggaggt ttggcggaac agtgatcagg aaccctctct ccaggaattc   8280
cactcatgaa atgtactacg tgtctggagc ccgcagcaat gtcacattta ctgtgaacca   8340
aacatcccgc ctcctgatga ggagaatgag gcgtccaact ggaaaagtga ccctggaggc   8400
tgacgtcatc ctcccaattg ggacacgcag tgttgagaca gacaagggac ccctggacaa   8460
agaggccata gaagaaaggg ttgagaggat aaaatctgag tacatgacct cttggtttta   8520
tgacaatgac aaccctaca ggacctggca ctactgtggc tcctatgtca caaaacctc    8580 aggaagtgcg gcgagcatgg taaatggtgt tattaaaatt ctgacatatc catgggacag   8640
gatagaggag gtcacaagaa tggcaatgac tgacacaacc ccttttggac agcaaagagt   8700
gtttaaagaa aaagttgaca ccagagcaaa ggatccacca gcgggaacta ggaagatcat   8760
gaaagttgtc aacaggtggc tgttccgcca cctggccaga gaaagaaacc ccagactgtg   8820
cacaaaggaa gaatttattg caaaagtccg aagtcatgca gccattggag cttacctgga   8880
agaacaagaa cagtggaaga ctgccaatga ggctgtccaa gacccaaagt tctgggaact   8940
ggtggatgaa gaaaggaagc tgcaccaaca aggcaggtgt cggacttgtg tgtacaacat   9000
gatgggaaaa agagagaaga agctgtcaga gtttggaaaa gcaaagggaa gccgtgccat   9060
atggtatatg tggctgggag cgcggtatct tgagtttgag gccctgggat tcctgaatga   9120
ggaccattgg gcttccaggg aaaactcagg aggaggagtg gaaggcattg gcttacaata   9180
cctaggatat gtgatcagag acctggctgc aatggatggt ggtggattct acgcggatga   9240
caccgctgga tgggacacgc gcatcacaga ggcagacctt gatgatgaac aggagatctt   9300
gaactacatg agcccacatc acaaaaaact ggcacaagca gtgatggaaa tgacatacaa   9360
gaacaaagtg gtgaaagtgt tgagaccagc cccaggaggg aaagcctaca tggatgtcat   9420
aagtcgacga gaccagagag gatccgggca ggtagtgact tatgctctga acaccatcac   9480
caacttgaaa gtccaattga tcagaatggc agaagcagag atggtgatac atcaccaaca   9540
tgttcaagat tgtgatgaat cagttctgac caggctggag gcatggctca ctgagcacgg   9600
atgtgacaga ctgaagagga tggcggtgag tggagacgac tgtgtggtcc ggcccatcga   9660
tgacaggttc ggcctggccc tgtcccatct caacgccatg tccaaggtta aaaggacat    9720 atctgaatgg cagccatcaa aagggtggaa tgattgggag aatgtgccct tctgttccca   9780
ccacttccat gaactacagc tgaaggatgg caggaggatt gtggtgcctt gccgagaaca   9840
ggacgagctc attgggagag aagggtgtc tccaggaaac ggctggatga tcaaggaaac   9900
agcttgcctc agcaaagcct atgccaacat gtggtcactg atgtatttc acaaaaggga    9960 catgaggcta ctgtcattgg ctgtttcctc agctgttccc acctcatggg ttccacaagg  10020
acgcacaaca tggtcgattc atgggaaagg ggagtggatg accacggaag acatgcttga  10080
ggtgtggaac agagtatgga taaccaacaa cccacacatg caggacaaga caatggtgaa  10140
aaaatgagaa gatgtccctt atctaaccaa gagacaagac aagctgtgcg gatcactgat  10200
tggaatgacc aatagggcca cctgggcctc ccacatccat ttagtcatcc atcgtatccg  10260
aacgctgatt ggacaggaga aatacactga ctacctaaca gtcatggaca ggtattctgt  10320
ggatgctgac ctgcaactgg gtgagcttat ctgaaacacc atctaacagg aataaccggg  10380
```

-continued

| | |
|---|---|
| atacaaacca cgggtggaga accggactcc ccacaacctg aaaccgggat ataaaccacg | 10440 |
| gctggagaac cgggctccgc acttaaaatg aaacagaaac cgggataaaa actacggatg | 10500 |
| gagaaccgga ctccacacat tgagacagaa gaagttgtca gcccagaacc ccacacgagt | 10560 |
| tttgccactg ctaagctgtg aggcagtgca ggctgggaca gccgacctcc aggttgcgaa | 10620 |
| aaacctggtt tctgggacct cccaccccag agtaaaaaga acggagcctc cgctaccacc | 10680 |
| ctcccacgtg gtggtagaaa gacggggtct agaggttaga ggagaccctc cagggaacaa | 10740 |
| atagtgggac catattgacg ccagggaaag accggagtgg ttctctgctt ttcctccaga | 10800 |
| ggtctgtgag cacagtttgc tcaagaataa gcagaccttt ggatgacaaa cacaaaacca | 10860 |
| ct | 10862 |

<210> SEQ ID NO 8
<211> LENGTH: 10707
<212> TYPE: DNA
<213> ORGANISM: Dengue virus type 3

<400> SEQUENCE: 8

| | |
|---|---|
| agttgttagt ctacgtggac cgacaagaac agtttcgact cggaagcttg cttaacgtag | 60 |
| tgctaacagt tttttattag agagcagatc tctgatgaac aaccaacgga agaagacggg | 120 |
| aaaaccgtct atcaatatgc tgaaacgcgt gagaaaccgt gtgtcaactg gatcacagtt | 180 |
| ggcgaagaga ttctcaaaag gactgctgaa cggccaggga ccaatgaaat tggttatggc | 240 |
| gttcatagct ttcctcagat ttctagccat tccaccaaca gcaggagtct tggctagatg | 300 |
| gggaaccttc aagaagtcgg gggccattaa ggtcctgaaa ggcttcaaga aggagatctc | 360 |
| aaacatgctg agcataatca acaaacggaa aagacatcg ctctgtctca tgatgataat | 420 |
| gccagcagca cttgctttcc acttgacttc acgagatgga gagccgcgca tgattgtggg | 480 |
| gaagaatgaa agaggaaaat ccctactttt taagacagcc tctggaatta acatgtgcac | 540 |
| actcatagcc atggacttgg agagatgtg tgatgacacg gtcacttaca aatgcccca | 600 |
| cattaccgaa gtggaacctg aagacattga ctgctggtgc aaccttacat caacatgggt | 660 |
| gacttatgga acgtgcaatc aagccggaga gcgtagacgc gacaagagat cagtggcgtt | 720 |
| agctccccat gtcggcatgg gactagacac acgcacccaa acctggatgt cggctgaagg | 780 |
| agcttggagg caagtcgaga aggtagagac atgggcccttt aggcacccag ggttcaccat | 840 |
| actagcccta tttcttgccc attacatagg cacatccttg acccagaagg tggttatttt | 900 |
| tatactacta atgctggtca ccccatccat gacaatgaga tgtgtgggag taggaaacag | 960 |
| agattttgtg gaaggtctat caggagctac gtgggttgac gtggtgctcg agcacggggg | 1020 |
| gtgtgtgact accatggcta agaacaagcc aacgttggat atagagcttc agaagaccga | 1080 |
| ggccacccaa ttggcgaccc taaggaagct atgcattgag gggaaaatta ccaacataac | 1140 |
| aactgactca gatgtcctta cccaagggga agcggttttg cctgaggagc aggaccagaa | 1200 |
| ctacgtgtgt aagcatacat acgtagacag aggctggggg aacggatgtg gtttgtttgg | 1260 |
| caagggaagc ttggtaacat gtgcgaaatt caatgcctg gaaccaatag agggaaaagt | 1320 |
| ggtgcaatat gagaacctca atacaccgt catcatcaca gtgcacacag agatcaaca | 1380 |
| ccaggtggga aatgaaacgc agggagtcac ggctgagata acacctcagg catcaaccac | 1440 |
| tgaagccatc ttgcctgaat atggaacct tgggctagaa tgctcaccac ggacaggttt | 1500 |
| ggatttcaat gaaatgatct tgctaacaat gaagaacaaa gcatggatgg tacatagaca | 1560 |
| atggttttttt gacctacctc taccatggac atcaggagct acaacggaaa caccaacctg | 1620 |

```
gaacaggaag gagcttcttg tgacatttaa aaacgcacat gcgaaaaaac aagaagtagt   1680
tgtccttgga tcgcaagagg gagcaatgca taccgcattg acaggagcca cagaaatcca   1740
aaactcagga ggcacaagta tttttgcggg gcacttaaaa tgtagactta agatggacaa   1800
attggaactc aaggggatga gctatgcaat gtgcacgaat acctttgtgt tgaagaaaga   1860
agtctcagaa acgcagcatg ggacaatact cattaaggtc gagtacaaag gggaagatgc   1920
accttgcaag attcctttct ccacagagga tggacaaggg aaagctcaca atggcagact   1980
gattacagcc aacccagtgg tgactaagaa ggaggagcct gtcaatattg aggctgaacc   2040
tccttttggg gaaagtaata tagtgattgg aattggagac aacgccttga aaatcaactg   2100
gtataagaaa ggaagctcta ttgggaagat gttcgaggcc actgccagag gtgcaaggcg   2160
catggccatc ttgggagaca cagcttggga ctttggatca gtgggtggtg ttctgaactc   2220
attaggcaaa atggtgcacc aaatattcgg aagtgcttac acagccctat tcagtggagt   2280
ctcttgggta tgaaaatcg gaataggagt tctcttgact tggatagggt tgaattcaaa   2340
aaacacatcc atgtcatttt catgcattgc gataggaatc atcacactct atctgggagc   2400
tgtggtgcaa gctgacatgg gatgtgttat aaactgaaaa ggcaaagaac tcaaatgtgg   2460
aagtggaatc ttcgtcacca acgaggtcca tacctggaca gagcaataca aattccaagc   2520
agactcccca aaaagattgg cgacagccat tgcaggcgct tgggagaatg gagtgtgcgg   2580
aattaggtca caaccagaa tggagaatct cctgtggaag caaatagcca atgaactgaa   2640
ctacatattg tgggaaaaca atatcaaatt aacggtagtt gtgggcgata taattggggt   2700
cttagagcaa ggaaaaagaa cactaacacc acaacccatg gagctaaaat actcatggaa   2760
aacgtgggga aaggcaaaaa tagtgacagc tgaaacacaa aattcctctt tcataataga   2820
cgggccaaac acgccggagt gtccaagtgc ctcaagagca tggaatgtgt gggaggtgga   2880
agattacggg ttcggagtct tcacaaccaa catatggctg aaactccgag aggtgtacac   2940
ccaactatgt gaccataggc taatgtcggc agctgttaag gatgagaggg ccgtacatgc   3000
cgacatgggc tattggatag aaagccaaaa gaatggaagt tggaagctag aaaaagcatc   3060
cctcatagag gtgaaaacct gcacatggcc aaaatcacat acccttttgg gtaatggtgt   3120
gctagagagt gacatgatca tcccaaagag tctagctggt cctatttcgc aacacaacca   3180
caggcccggg taccacaccc agacggcggg accctggcat ttaggaaaat tagagctgga   3240
cttcaactat tgtgaaggaa caacagttgt catcacagaa aactgtggga caagaggccc   3300
atcattgaga acaacaacag tgtcaggaa gttaatacac gaatggtgtt gccgttcgtg   3360
cacacttcct cccttgcgat acatgggaga agacggttgc tggtatggca tggaaatcag   3420
acccatcagt gagaaagaag agaacatggt aaagtcttta gtctcagcgg gaagtggaaa   3480
ggtggacaac ttcacaatgg gtgtcttgtg tttggcaatc ctctttgaag aggtgatgag   3540
aggaaaattt gggaagaaac acatgattgc ggggtttttc ttcacgtttg tgctccttct   3600
ctcagggcaa ataacatgga gagacatggc gcacacacta ataatgattg gtccaacgc   3660
atctgacagg atgggaatgg gcgttaccta cctagcttta attgcaacat ttaaaatcca   3720
gccattcttg gctttgggat ttttcctaag aaaactgaca tccagagaaa atttattgtt   3780
aggagttggg ctggctatgg caacaacgtt acaactgcca gaggacattg aacaaatggc   3840
aaatggaatc gctctggggc tcatggctct taaactgata acacaatttg aaacatacca   3900
attatggaca gcattaatct ccttaacgtg ttcaaataca atgtttacgt tgactgttgc   3960
ctggagaaca gccaccctga ttttggccgg agtttcgctt ttaccagtgt gccagtcttc   4020
```

```
gagcatgagg aaaacagact ggcttccaat ggcagtggca gctatgggag ttccacctct    4080 accactttt attttagct tgaaagacac acttaaaagg agaagctggc cactgaatga    4140
aggggtgatg gctgttgggc ttgtgagcat tctggccagt tctctcctta gaaatgatgt    4200
acccatggct ggaccattag tggccggggg cttgctgata gcgtgctacg tcataactgg    4260
cacgtcagca gacctcaccg tagaaaagc agcagatata acatgggagg aagaggctga    4320
gcaaacagga gtgtcccaca acttaatgat cacagttgat gatgatgaa caatgagaat    4380 aaaagatgat gagactgaga atatcctaac agtgcttttg aaaacagcat tactaatagt    4440
atcaggagtc tttccatact ccatacccgc aacattgctg gtctggcata cttggcaaaa    4500
gcaaacccaa agatccggcg ttctatggga cgtacccagc cccccagaga cacagaaagc    4560
agaactggaa aaggggtct ataggatcaa acagcaagga attttggga aaacccaagt    4620 aggggttgga gtacagaaag aaggagtctt ccacaccatg tggcacgtta caagaggggc    4680
agtgttgaca tataatggga aaagactgga accgaactgg gctagcgtga aaaaagatct    4740
gatttcatac ggaggaggat ggagattgag cgcacaatgg caaaggggg aggaggtgca    4800 ggttattgcc gtagagcctg gaagaacccc aaagaacttt caaaccatgc caggcacttt    4860
tcagactaca acagggaaa taggagcaat tgcactggat ttcaagcctg aacttcagg    4920 atctcctatc ataaacagag agggaaaggt agtgggactg tatggcaatg gagtggttac    4980
aaagaatggt ggctacgtca gcggaatagc gcaaacgaat gcagaaccag atggaccgac    5040
accagaattg gaagaagaga tgttcaaaaa gcgaaatcta accataatgg atcttcatcc    5100
tgggtcagga aagacacgga aatacctccc agctattgtt agagaggcaa tcaagagacg    5160
tttaagaact ctaattttgg caccgacaag ggtggttgca gctgagatgg aagaagcatt    5220 gaagggctc ccaataaggt accaacaac agcaacaaaa tctgaacaca caggaagaga    5280
gattgttgat ctaatgtgcc acgcaacgtt cacaatgcgt ctgctgtcac cagttagggt    5340
tccaaactat aacttgataa taatggatga agcccatttc acagacccag ccagtatagc    5400
ggctagaggg tacatatcga ctcgtgttgg aatgggagag gcagccgcaa ttttcatgac    5460
agcaacgccc cctggaacag ctgatgcctt tcctcagagc aacgctccaa ttcaagatga    5520
agaaagggac ataccagaac gctcatggaa ttcaggcaat gaatggatta ccgacttcgc    5580
tgggaaaacg gtgtggtttg tccccagcat taaagccgga aatgacatag caaactgctt    5640
gcggaaaaac gggaaaaagg tcattcaact tagtaggaag acttttgaca cagaatatca    5700
gaaaactaaa ctgaatgatt gggacttcgt ggtgacaact gacatttcag aaatggggc    5760 caatttcaaa gcagatagag tgatcgaccc aagaagatgt ctcaaaccag tgatcctgac    5820
agatggacca gagcgggtga tcctggctgg accaatgcca gtcaccgcgg cgagtgctgc    5880
gcaaaggaga gggagagttg gcaggaaccc acaaaaagaa aatgaccagt acatattcac    5940
gggccagcct ctcaacaatg atgaagacca tgctcactgg acagaagcaa aaatgctgct    6000
ggacaacatt aatacaccag aagggatcat accagctctc tttgagccag aaagggagaa    6060
gtcagccgcc atagacggtg agtatcgctt gaaaggtgag tccaggaaga ctttcgtgga    6120
actcatgagg aggggtgacc ttccagtctg gttagcccat aaagtagcat cagaagggat    6180
caaatataca gatagaaat ggtgctttga tggacaacgt aataatcaaa ttttagga    6240 gaacatggat gtggaaatct ggacaaagga aggagaaag aaaaaattga gacctaggtg    6300
gcttgatgcc cgcacttatt cagatccctt agcactcaag gaattcaagg actttgcggc    6360
tggcagaaag tcaatcgccc ttgatcttgt gacagaaata ggaagagtgc cttcacacct    6420
```

```
agcccataga acgagaaacg ctctggacaa tctggtgatg ctgcatacgt cagaacatgg    6480
cggtagggcc tacaggcatg cggtggagga actaccagag acaatggaaa cactcctact    6540
cttgggactc atgatcttgt tgacaggtgg agcaatgctt ttcttaatat caggtaaagg    6600
gattggaaag acttcaatag gactcatttg tgtaattgct tccagcggca tgttgtggat    6660
ggccgaaatc ccactccaat ggatcgcgtc ggctatagtc ctggagtttt ttatgatggt    6720
gttgcttata ccagaaccag aaaagcagag aaccccccaa gacaaccaac tcgcatatgt    6780
cgtgataggc atacttacat tggctgcaat aatagcagcc aatgaaatgg gattgttgga    6840
aactacaaag agagatttag gaatgtctaa ggagccaggt gttgtctctc caaccagcta    6900
tttagatgtg gacttgcacc cagcatcagc ctggacattg tacgccgtgg ccactacagt    6960
aataacacca atgttaagac ataccataga gaattctaca gcaaatgtgt ctctggcagc    7020
tatagccaac caggcagtgg tcctgatggg tttggacaaa ggatggccaa tatcaaaaat    7080
ggacttagga gtacccctac tggcattggg ttgctattca caagtgaacc cactgactct    7140
aacagcggca gtactcttgc tgatcacaca ttatgctatt ataggtccag gattgcaggc    7200
aaaagccact cgtgaagctc agaaaaggac agctgctgga ataatgaaga tccaacggt    7260 ggatgggata atgacaatag acctagatcc tgtaatatat gattcaaaat ttgaaaagca    7320
actgggacag ttatgctcc tggttttgtg tgcagttcaa cttttgttaa tgagaacatc    7380
atgggccttg tgtgaagctt taactctagc tacaggacca ataacaacac tctgggaagg    7440
atcacctggg aagttttgga acaccacgat agctgtttcc atggcgaaca ttttagagg    7500 gagctattta gcaggagctg ggcttgcttt ttctattatg aaatcagttg gaacaggaaa    7560
aagaggaaca ggctcacaag gtgaaacctt aggagaaaaa tggaaaaaga attaaatca    7620 attatcccgg aaagagtttg acctttacaa gaaatctgga atcactgaag tggatagaac    7680
agaagccaaa gaagggttga aaagaggaga ataacacat catgccgtgt ccagaggtag    7740
cgcaaaactt caatggtttg tggagagaaa catggtcatt cccgaaggaa gagtcataga    7800
cttgggctgt ggaagaggag ctggtcata ttactgtgca ggactgaaaa agtcacaga    7860 agtgcgagga tacacaaaag gcggtccagg acacgaagaa ccagtaccca tgtccacata    7920
tggatggaac atagttaagt taatgagtgg aaaggatgtg ttttatcttc cacctgaaaa    7980
gtgtgacacc ctgttgtgtg acattggaga atcttcacca agcccaacag tggaagaaag    8040
cagaactata agagttttga gatggttga accatggcta agaacaacc aattttgcat    8100 taaagtattg aaccttaca tgccaactgt gattgagcac ctagaaagac tacaaaggaa    8160
acatggagga atgcttgtga gaatccact ttcacgaaac tccacgcacg aaatgtactg    8220
gatatctaat ggcacaggta acattgtcgc ttcagtcaat atggtatcta gactgctact    8280
gaacaggttc acgatgacac acagaagacc caccattgag aaagatgtgg atttaggagc    8340
aggaactcga catgttaatg cggaaccaga acacccaac atggatgtca ttggggaaag    8400
aataaaaagg atcaaggagg agcataattc aacatggcac tatgatgacg aaaaccccta    8460
caaaacgtgg gcttaccatg gatcttatga agtcaaagcc acaggctcag cctcctccat    8520
gataaatgga gtcgtgaaac tcctcactaa accatgggat gtggtgccca tggtgacaca    8580
gatggcaatg acagatacaa ctccatttgg ccagcagaga gtctttaaag agaaagtgga    8640
caccaggaca cccaggtcca tgccaggaac aagaagggtc atgggatca cagcggagtg    8700 gctctggaga accctgggaa ggaacaaaaa acccaggtta tgcacaaggg aagagtttac    8760
aaaaaaggtc agaactaacg cagccatggg cgccgttttc acagaggaga accaatggga    8820
```

-continued

```
cagcgcgaaa gctgctgttg aggatgagga tttttggaaa cttgtggaca gagaacgtga   8880
actccacaaa ttgggcaagt gtggaagctg tgtttacaac atgatgggca agagagagaa   8940
gaaacttgga gagtttggca aagcaaaagg cagtagagct atatggtaca tgtggttggg   9000
agccaggtac cttgagttcg aagcccttgg attcttaaat gaagaccact ggttctcgcg   9060
tgagaactct tacagtggag tggaaggaga aggactgcac aagctaggct atatattaag   9120
ggacatttcc aagatacccg gaggagctat gtatgctgat gacacagctg gttgggacac   9180
aagaataaca gaagatgacc tgcacaatga ggaaaagatc acacagcaaa tggaccctga   9240
acacaggcag ttagcgaacg ctatatttaa gctcacatac caaaacaaag tggtcaaagt   9300
tcaacgaccg actccaacag gcacggtaat ggacatcata tctaggaaag accaaagagg   9360
cagtggacag gtaggaactt atggtctgaa tacattcacc aacatggaag cccagttaat   9420
cagacaaatg gaaggagaag gtgtgctgtc aaaggcagac ctcgagaacc ctcatctgcc   9480
agagaagaaa attacacaat ggttggaaac caaaggagtg gagaggttaa aaagaatggc   9540
cattagcggg gatgattgcg tagtgaaacc aatcgatgac aggttcgcta atgccctgct   9600
cgctctgaac gatatgggga aggttcggaa agacatacct caatggcagc catcaaaggg   9660
atggcatgat tggcaacagg ttcctttctg ctcccaccac tttcatgaat tgatcatgaa   9720
agatggaaga aagttggtgg ttccctgcag accccaggac gaactaatag gaagagcaag   9780
aatctctcaa ggagcgggat ggagccttag agaaaccgca tgtctgggga aagcctacgc   9840
tcaaatgtgg agtctcatgt attttcacag aagagacctc agactagcat ccaacgccat   9900
atgttcagca gtaccagtcc actgggtccc cacaagtaga acgacatggt ctattcatgc   9960
tcaccatcag tggatgacca cagaagacat gcttactgtc tggaacaggg tgtggatcga  10020
ggacaatcca tggatggaag acaaaactcc agtcacaacc tgggaaaatg ttccatatct  10080
agggaagaga gaagaccaat ggtgcggatc acttattggt ctcacttcca gagcaacctg  10140
ggcccagaac atacccacag caattcaaca ggtgagaagc cttataggca atgaagagtt  10200
tctggactac atgccttcaa tgaagagatt taggaaggag gaggagtcgg agggagccat  10260
ttggtaaacg taggaagtga aaaagaggtt aactgtcagg ccacattaag ccacagtacg  10320
gaagaagctg tgctgcctgt gagccccgtc caaggacgtt aaaagaagaa gtcaggcccc  10380
aaagccacgg tttgagcaaa ccgtgctgcc tgtagctccg tcgtggggac gtaaaacctg  10440
ggaggctgca aactgtggaa gctgtacgca cggtgtagca gactagcggt tagaggagac  10500
ccctcccatg acacaacgca gcagcggggc ccgagcactg agggaagctg tacctccttg  10560
caaaggacta gaggttagag gagacccccc gcaaataaaa acagcatatt gacgctggga  10620
gagaccagag atcctgctgt ctcctcagca tcattccagg cacagaacgc cagaaaatgg  10680
aatggtgctg ttgaatcaac aggttct                                     10707

<210> SEQ ID NO 9
<211> LENGTH: 10735
<212> TYPE: DNA
<213> ORGANISM: Dengue virus type 1 (LAV1)

<400> SEQUENCE: 9
agttgttagt ctacgtggac cgacaagaac agtttcgaat cggaagcttg cttaacgtag     60
ttctaacagt tttttattag agagcagatc tctgatgatc aaccaacgaa aaaagacggg    120
tcgaccgtct ttcaatatgc tgaaacgcgc gagaaaccgc gtgtcaactg tttcacagtt    180
ggcgaagaga ttctcaaaag gattgctctc aggccaagga cccatgaaat tggtgatggc    240
```

```
tttcatagca ttcttaagat ttctagccat acccccaaca gcaggaattt tggctagatg    300
gggctcattc aagaagaatg gagcgattaa agtgttacgg ggtttcaaga gagaaatctc    360
aaacatgcta aacataatga acaggaggaa aagatccgtg accatgctcc ttatgctgct    420
gcccacagcc ctggcgttcc atctgacgac acgagggggga gagccgcata tgatagttag    480
caagcaggaa agaggaaagt cacttttgtt caagacctct gcaggtgtca acatgtgcac    540
cctcattgcg atggatttgg gagagttgtg tgaggacacg atgacctaca aatgcccccg    600
gatcactgag gcggaaccag atgacgttga ctgttggtgc aatgccacgg acacatgggt    660
gacctatgga acgtgctctc aaactggcga acaccgacga gacaaacgtt ccgtcgcatt    720
ggccccacac gtggggcttg cctagaaac aagagccgaa acgtggatgt cctctgaagg    780
tgcttggaaa cagatacaaa aagtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaacaaacc aacactggac attgaactct gaagacggaa    1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
cttttgtgtgc cgacgaacgt tcgtggacag aggctggggc aatggctgtg ggctattcgg   1260
aaaaggtagt ctaataacgt gtgccaagtt taagtgtgtg acaaaactag aaggaaagat   1320
agctcaatat gaaaacctaa aatattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aacccttaca ttagattgtt cacctaggac   1500
agggctagat tttaacgaga tggtgttgct gacaatgaaa aagaaatcat ggcttgtcca   1560
caaacagtgg tttctagact taccactgcc ttggaccctct ggggctttaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc cttttcgac ccaagatgag aaaggagcaa cccagaatgg   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaggaa gcagcatagg aaaatgttt gaagcaactg cccgaggagc   2160
acgaaggatg gccattctgg gagacaccgc atgggactc ggttctatag gaggagtgtt   2220
cacgtctatg ggaaaactgg tacaccaggt ttttggaact gcatatggag ttttgttag   2280
cggagttctt tggaccatga aaataggaat aggggatctg ctgacatggc taggattaaa   2340
ttcaaggaac acgtccctt cggtgatgtg catcgcagtt ggcatggtca cactgtacct   2400
aggagtcatg gttcaggcag attcgggatg tgtaatcaac tggaaaggca gagaacttaa   2460
atgtggaagc ggcattttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga gaacatcatg tggaaacaaa tatcaaatga   2640
```

```
attgaaccac atcctacttg aaaatgacat gaaatttaca gtggtcgtgg gagacgttag    2700
tggaatcttg gcccaaggga aaaaaatgat taggccacaa cccatggaac acaaatactc    2760
gtggaaaagc tggggaaaag ctaaaatcat aggagcggat gtacagaaca ccaccttcat    2820
catcgacggc ccaaacaccc cagaatgccc tgacaatcaa agagcatgga atatttggga    2880
agtagaggac tatggatttg ggattttcac gacaaacata tggttgaaat gcgtgactc     2940 ctacacccaa gtatgtgacc accggctgat gtcagctgcc attaaggaca gcaaggcagt    3000
ccatgctgac atggggtact ggatagaaag tgaaagaaac gagacatgga agttggcgag    3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag caagttgga     3240 actagatttc gattttgtg aaggtaccac agttgttgtg atgaacatt gtggaaatcg      3300 aggaccatct ctcagaacca caacagtcac aggaaagata tccatgaat ggtgctgcag    3360 atcttgtacg ctaccccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga acactggctg tgttcctcct    3600
tcttataatg ggacaattga catggagtga tctgatcagg ttatgtatta tggttggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta taacagaaaa caaaatctgg ggaaggaaga gttggcccct    4140
caatgaagga attatggctg ttggaatagt tagtattcta ctaagttcac ttttaaaaaa    4200
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
gaagatcaaa gatgaagaga gagatgacac gctcaccatt ctccttaaag caactctgct    4440
ggcagtctca ggggtgtacc caatgtcaat accagcgacc cttttgtgt ggtatttttg     4500 gcagaaaaag aaacagagat caggagtgct atgggacaca cccagcccccc cagaagtgga    4560 aagagcagtt cttgatgatg gcatctatag aattttgcaa agaggactgt gggcaggtc     4620 ccaagtagga gtaggagttt ccaagaaggg cgtgttccac acaatgtggc acgtcactag    4680
gggagctgtc ctcatgtatc aaggaaaaag gctggaacca agctgggca gtgtcaaaaa     4740 agacttgatc tcatatggag gaggttggag gtttcaagga tcctggaaca cgggagaaga    4800
agtacaggtg attgctgttg aaccggaaaa aaacccaaa aatgtacaaa caacgccggg     4860
taccttcaag acccctgaag gcgaagttgg agccatagcc ttagacttta aacctggcac    4920
atctggatct cccatcgtaa acagagaggg aaaaatagta ggtctttatg gaaatggagt    4980
ggtgacaaca agcggaactt acgttagtgc catagctcaa gctaaggcat cacaagaagg    5040
```

```
gcctctacca gagattgagg acaaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggccttccca cagagcaatg caattatcca   5520
agatgaggaa agagacattc ctgagagatc atggaactca ggctatgact ggatcactga   5580
tttttccagg t aaaacagtct ggtttgttcc aagcatcaaa tcaggaaatg acattgccaa   5640
ctgtttaaga aaaaacggga acgggtgat ccaattgagc agaaaaacct ttgacactga   5700
gtaccgaaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa acaatgatga ggaccacgct cattggacag aagcaaagat   6000
gctccttgac aatataaaca caccagaagg gattatccca gccctctttg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaaatagggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa cgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcgtgat attgacagtg gcagccaatg agatgggatt   6840
attggaaacc acaaagaaag acctgggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaagaaca gcggctggaa taatgaaaaa   7260
tccaactgtc gacgggattg ttgcaataga cttagatccc gtggtttacg atgcaaaatt   7320
tgaaaaacag ctaggccaaa taatgttgtt gatactttgc acatcacaga ttcttttgat   7380
gcggactaca tgggccttgt gtgaatccat cacattggct actggacctc tgaccactct   7440
```

```
ttgggaggga tctccaggaa aattctggaa caccacaata gcggtatcca tggcaaacat    7500 tttcagggg  agttatctag caggagcagg tctggccttc tcattaatga aatctctagg    7560
aggaggtagg agaggcacgg gagcccaagg ggaaacactg ggagaaaaat ggaaaagaca    7620
actaaaccaa ctgagcaagt cagaattcaa tacttacaag aggagtggga ttatggaggt    7680
ggatagatcc gaagccaaag agggactgaa aagaggagaa acaaccaaac acgcagtatc    7740
gagaggaacg gccaaactga ggtggttcgt ggagaggaac cttgtgaaac cagaagggaa    7800
agtcatagac ctcggttgtg gaagaggtgg ctggtcatat tattgcgctg ggctgaagaa    7860
agtcacagaa gtgaaaggat acacaaaagg aggacctgga catgaggaac caatcccaat    7920
ggcgacctat ggatggaacc tagtaaagct gcactccgga aaagatgtat tttttatacc    7980
acctgagaaa tgtgacaccc ttttgtgtga tattggtgag tcctctccga acccaactat    8040
agaggaagga agaacgttac gtgttctgaa aatggtggaa ccatggctca gaggaaacca    8100
attttgcata aaaattctaa atccctatat gccgagcgtg gtagaaactc tggaacaaat    8160
gcaaagaaaa catggaggaa tgctagtgcg aaacccactc tcaagaaatt ccacccatga    8220
aatgtactgg gtttcatgtg gaacaggaaa cattgtgtca gcagtaaaaca tgacatctag    8280 aatgttgcta aatcggttca caatggctca caggaagcca acatatgaaa gagacgtgga    8340
cttaggcgct ggaacaagac atgtggcagt agaaccagag gtagccaacc tagatatcat    8400
tggccagagg atagagaata taaaaaatga acataagtca acatggcatt atgatgagga    8460
caatccatac aaaacatggg cctatcatgg atcatatgag gttaagccat caggatcggc    8520
ctcatccatg gtcaatggcg tggtgagatt gctcaccaaa ccatgggatg ttatccccat    8580
ggtcacacaa atagccatga ctgataccac acccttt gga caacagaggg tgtttaaaga    8640
gaaagttgac acgcgcacac caaaagcaaa acgtggcaca gcacaaatta tggaagtgac    8700
agccaggtgg ttatggggtt ccttttctag aaacaaaaaa cccagaattt gcacaagaga    8760
ggagtttaca agaaaagtta ggtcaaacgc agctattgga gcagtgttcg ttgatgaaaa    8820
tcaatggaac tcggcaaaag aagcagtgga agacgaacgg ttctgggaac ttgtccacag    8880
agagagggag cttcataaac aggggaaatg tgccacgtgt gtctacaata tgatgggaa    8940 gagagagaaa aaattaggag agttcggaaa ggcaaaagga agtcgtgcaa tatggtacat    9000
gtggttggga gcacgcttcc tagagtttga agcccttggt ttcatgaatg aagatcactg    9060
gttcagtaga gagaattcac tcagtggagt ggaaggagaa ggactccaca acttggata    9120 catactcaga gacatatcaa ggattccagg ggggaacatg tatgcagatg acacagccgg    9180
atgggacaca gaataacag aggatgatct ccagaatgag gctaaaatca ctgacatcat    9240
ggagcccgaa catgccctgc tggctacgtc aatctttaag ctgacctacc aaaataaggt    9300
ggtaagggtg cagagaccag caaaaaatgg aaccgtgatg gatgttatat ccagacgtga    9360
ccagagaggc agtggacagg ttggaactta tggcttaaac actttcacca acatggaggc    9420
ccaactgata agacaaatgg agtctgaggg aatcttttta cccagcgaat ggaaaccccc    9480
aaatctagcc ggaagagttc tcgactggtt ggaaaaatat ggtgtcgaaa ggctgaaaag    9540
aatggcaatc agcggagatg actgtgtggt gaaaccaatt gatgacaggt tcgcaacagc    9600
cttaacagct ttgaatgaca tgggaaaagt aagaaaagac ataccacaat gggaaccttc    9660
aaaaggatgg aatgattggc aacaagtgcc tttctgttca caccacttcc accagctaat    9720
tatgaaggat gggagggaga tagtggtgcc atgccgcaac caagatgaac ttgtggggag    9780
ggccagagta tcacaaggcg ccggatggag cctgagagaa accgcatgcc taggcaagtc    9840
```

-continued

| | |
|---|---|
| atatgcacaa atgtggcagc tgatgtattt ccacaggaga gacctgagac tggcggctaa | 9900 |
| cgctatttgt tcagccgttc cagttgattg ggtcccaacc agccgcacca cctggtcgat | 9960 |
| ccatgcccat caccaatgga tgacaacaga agacatgtta tcagtatgga tagggtctg | 10020 |
| gatagaggaa aacccatgga tggaggataa gactcatgtg tccagttggg aagaagttcc | 10080 |
| atacctagga aagagggaag atcagtggtg tggatccctg ataggcttaa cagcaagggc | 10140 |
| cacctgggcc actaatatac aagtggccat aaaccaagtg agaaggctca ttgggaatga | 10200 |
| gaattatcta gattacatga catcaatgaa gagattcaag aatgagagtg atcccgaagg | 10260 |
| ggcactctgg taagtcaaca cattcacaaa ataaaggaaa ataaaaaatc aaatgaggca | 10320 |
| agaagtcagg ccagattaag ccatagtacg gtaagagcta tgctgcctgt gagccccgtc | 10380 |
| caaggacgta aaatgaagtc aggccgaaag ccacggtttg agcaagccgt gctgcctgtg | 10440 |
| gctccatcgt ggggatgtaa aaacccggga ggctgcaacc catggaagct gtacgcatgg | 10500 |
| ggtagcagac tagtggttag aggagacccc tcccaagaca caacgcagca gcggggccca | 10560 |
| acaccagggg aagctgtacc ctggtggtaa ggactagagg ttagaggaga ccccccgcgt | 10620 |
| aacaataaac agcatattga cgctgggaga gaccagagat cctgctgtct ctacagcatc | 10680 |
| attccaggca cagaacgcca gaaaatggaa tggtgctgtt gaatcaacag gttct | 10735 |

<210> SEQ ID NO 10
<211> LENGTH: 10723
<212> TYPE: DNA
<213> ORGANISM: Dengue virus type 2 (LAV2)

<400> SEQUENCE: 10

| | |
|---|---|
| agttgttagt ctacgtggac cgacaaagac agattctttg agggagctaa gctcaatgta | 60 |
| gttctaacag tttttttaatt agagagcaga tctctgatga ataaccaacg gaaaaaggcg | 120 |
| aaaaacacgc ctttcaatat gctgaaacgc gagagaaacc gcgtgtcgac tgtgcaacag | 180 |
| ctgacaaaga gattctcact tggaatgctg cagggacgag gaccattaaa actgttcatg | 240 |
| gccctggtgg cgttccttcg tttcctaaca atcccaccaa cagcagggat attgaagaga | 300 |
| tggggaacaa ttaaaaaatc aaaagctatt aatgttttga gagggttcag gaaagagatt | 360 |
| ggaaggatgc tgaacatctt gaataggaga cgcagatctg caggcatgat cattatgctg | 420 |
| attccaacag tgatggcgtt ccatttaacc acacgtaacg gagaaccaca catgatcgtc | 480 |
| agcagacaag agaaagggaa aagtcttctg tttaaaacag aggttggcgt gaacatgtgt | 540 |
| accctcatgg ccatggacct tggtgaattg tgtgaagaca caatcacgta caagtgtccc | 600 |
| cttctcaggc agaatgagcc agaagacata gactgttggt gcaactctac gtccacgtgg | 660 |
| gtaacttatg gacgtgtgta ccaccatggg aacatagaa gagaaaaaag atcagtggca | 720 |
| ctcgttccac atgtgggaat gggactggag acacgaactg aaacatggat gtcatcagaa | 780 |
| ggggcctgga aacatgtcca gagaattgaa acttggatct tgagacatcc aggcttcacc | 840 |
| atgatggcag caatcctggc atacaccata ggaacgacac atttccaaag agccctgatt | 900 |
| ttcatcttac tgacagctgt cactccttca atgacaatgc gttgcatagg aatgtcaaat | 960 |
| agagacttg tggaagggt tcaggagga agctggttg acatagtctt agaacatgga | 1020 |
| agctgtgtga cgacgatggc aaaaaacaaa ccaacattgg attttgaact gataaaaaca | 1080 |
| gaagccaaac agcctgccac cctaaggaag tactgtatag aggcaaagct aaccaacaca | 1140 |
| acaacagaat ctcgctgccc aacacaaggg gaacccagcc taatgaaga gcaggacaaa | 1200 |
| aggttcgtct gcaaacactc catggtagac agaggatggg gaaatggatg tggactattt | 1260 |

```
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaaggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat ccctttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt ggaggagtg   2220 tttacatcta taggaaaggc tctccaccaa gtctttggag caatctatgg agctgccttc   2280
agtgggcttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga ctggaaaaaa caaagaactg   2460 aaaatgtggca gtgggatttt catcacagac aacgtgcaca catggacaga acaatacaag   2520
ttccaaccag aatcccttc aaaactagct tcagctatcc agaaagccca tgaagaggac   2580 atttgtgaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga aaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca caggaacat gtcctttaga gacctgggaa gagtgatggt tatggtaggc   3660
```

```
gccactatga cggatgacat aggtatgggc gtgacttatc ttgccctact agcagccttc    3720
aaagtcagac caacttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttttct aacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctc ttctaatgca taagggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag agatcgaaga tgacatttt cgaaagagaa gactgaccat catggacctc    5100
cacccaggag cggggaaagac gaagagatac cttccggcca tagtcagaga agctataaaa    5160
cggggtttga gaacattaat cttggccccc actagagttg tggcagctga aatggaggaa    5220
gcccttagag gacttccaat aagataccag accccagcca tcagagctgw gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggatttt    5460 atgacagcca ctcccccggg aagcagagac ccatttcctc agagcaatgc accaatcata    5520
gatgaagaaa gagaaatccc tgaacgctcg tggaattccg acatgaatg ggtcacggat    5580 tttaagggaa agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata daccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
```

```
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg gaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cggcatcat gaaaaaccca    7260 actgtcgatg gaataacagt gattgaccta gatccaatac cttatgatcc aaagtttgaa    7320
aagcagttgg gacaagtaat gctcctagtc ctctgcgtga ctcaagtatt gatgatgagg    7380
actacatggg ctctgtgtga ggctttaacc ttagctaccg ggcccatctc acattgtgg    7440 gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa agccgattg    7620 aacgcattgg gaaaaagtga attccagatc tacaagaaaa gtggaatcca ggaagtggat    7680
agaaccttag caaagaaggg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
```

```
cacccataca aaacgtgggc ataccatggt agctatgaaa caaaacagac tggatcagca    8520
tcatccatgg tcaacggagt ggtcaggctg ctgacaaaac cttgggacgt tgtcccatg    8580
gtgacacaga tggcaatgac agacacgact ccatttggac aacagcgcgt ttttaaagag    8640
aaagtggaca cgagaaccca agaaccgaaa gaaggcacga agaaactaat gaaaataaca    8700
gcagagtggc tttggaaaga attagggaag aaaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg aaggagaag ggctgcacaa gctaggttac    9120
attctaagag acgtgagcaa aaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc atttttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata cttttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtggagatga ttgtgttgtg aaacctttag atgacaggtt cgcaagcgct    9600
ttaacagctc taaatgacat gggaaagatt aggaaagaca tacaacatgg gaaccttca    9660
agaggatgga atgattggac acaagtgccc ttctgttcac accatttcca tgagttaatc    9720
atgaagacg tcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg    10020
attcaagaaa acccatggat ggaagacaaa actccagtgg aatcatggga ggaaatccca    10080
tacttgggga aaagaagaa ccaatggtgc ggctcattga ttgggttaac aagcagggcc    10140
acctgggcaa gaacatcca agcagcaata aatcaagtta gatcccttat aggcaatgaa    10200
gaatacacag attacatgcc atccatgaaa agattcagaa gagaagagga agagcagga    10260
gttctgtggt agaaagcaaa actaactga aacaaggcta gaagtcaggt cggattaagc    10320
catagtacgg aaaaaactat gctacctgtg agccccgtcc aaggacgtta aaagaagtca    10380
ggccatcata aatgccatag cttgagtaaa ctatgcagcc tgtagctcca cctgagaagg    10440
tgtaaaaaat ccgggaggcc acaaaccatg gaagctgtac gcatggcgta gtggactagc    10500
ggttagagga gaccccctccc ttacaaatcg cagcaacaat gggggcccaa ggcgagatga    10560
agctgtagtc tcgctggaag gactagaggt tagaggagac cccccgaaa caaaaaacag    10620
catattgacg ctgggaaaga ccagagatcc tgctgtctcc tcagcatcat tccaggcaca    10680
gaacgccaga aaatggaatg gtgctgttga atcaacaggt tct                       10723
```

<210> SEQ ID NO 11
<211> LENGTH: 10699
<212> TYPE: DNA

<213> ORGANISM: Dengue virus type 3 (LAV3)

<400> SEQUENCE: 11

```
agttgttagt ctacgtggac cgacaagaac agtttcgact cggaagcttg cttaacgtag      60
tgctgacagt tttttattag agagcagatc tctgatgaac aaccaacgga aaagacggg      120
aaaaccgtct atcaatatgc tgaaacgcgt gagaaaccgt gtgtcaactg gatcacagtt     180
ggcgaagaga ttctcaagag gattgctgaa cggccaagga ccaatgaaat tggttatggc    240
atttatagct ttcctcagat ttctagccat tccaccgaca gcaggagtct tggctagatg    300
gggtaccttt aagaagtcgg gggctattaa ggtcttaaaa gcttcaaga aggagatctc     360
aaacatgctg agcattatca acaaacggaa aaagacatcg ctctgtctca tgatgatgtt   420
accagcaaca cttgctttcc acttaacttc acgagatgga gagccgcgca tgattgtggg    480
gaagaatgaa agaggaaaat ccctactttt caagacagcc tctggaatca acatgtgcac    540
actcatagct atggatctgg agagatgtg tgatgacacg gtcacttaca atgcccca      600
cattaccgaa gtggagcctg aagacattga ctgctggtgc aaccttacat cgacatgggt    660
gacttatgga acatgcaatc aagctggaga gcatagacgc gataagagat cagtggcgtt    720
agctccccat gttggcatgg gactggacac acgcactcaa acctggatgt cggctgaagg    780
agcttggaga caagtcgaga aggtagagac atgggccctt aggcacccag ggtttaccat    840
actagcccta tttcttgccc attacatagg cacttccttg acccagaaag tggttatttt    900
tatactatta atgctggtta ccccatccat gacaatgaga tgtgtaggag taggaaacag    960
agattttgtg gaaggcctat cgggagctac gtgggttgac gtggtgctcg agcacggtgg   1020
gtgtgtgact accatggcta agaacaagcc cacgctggac atagagcttc agaagaccga   1080
ggccacccaa ctggcgaccc taaggaagct atgcattgag ggaaaaatta ccaacataac   1140
aaccgactca agatgtccca cccaagggga agcgatttta cctgaggagc aggaccagaa   1200
ctacgtgtgt aagcatacat acgtggacag aggctgggga aacggttgtg gtttgtttgg   1260
caagggaagc ttggtgacat gcgcgaaatt tcaatgttta gaatcaatag agggaaaagt   1320
ggtgcaacat gagaacctca aataccacgt catcatcaca gtgcacacag agaccaaca   1380
ccaggtggga aatgaaacgc agggagtcac ggctgagata caccccagg catcaaccgc   1440
tgaagccatt ttacctgaat atggaaccct cgggctagaa tgctcaccac ggacaggttt   1500
ggatttcaat gaaatgatct yattgacaat gaagaacaaa gcatggatgg tacatagaca   1560
atggttcttt gacttacccc taccatggac atcaggagct acagcagaaa caccaacttg   1620
gaacaggaaa gagcttcttg tgacatttaa aaatgcacat gcaaaaaagc aagaagtagt   1680
tgttcttgga tcacaagagg gagcaatgca tacagcactg acaggagcta cagagatcca   1740
aacctcagga ggcacaagta tctttgcggg gcacttaaaa tgtagactca agatggacaa   1800
attggaactc aaagggatga gctatgcaat gtgcttgggt agctttgtgt tgaagaaaga   1860
agtctccgaa acgcagcatg gacaatact cattaaggtt gagtacaaag ggaaagatgc   1920
accctgcaag attcctttct ccacggagga tggacaagga aagctcaca atggcagact   1980
gatcacagcc aatccagtgg tgaccaagaa ggaggagcct gtcaacattg aggctgaacc   2040
tccttttgga gaaagtaaca tagtaattgg aattggagac aaagccctga aaatcaactg   2100
gtacaagaag ggaagctcga ttgggaagat gttcgaggct actgccagag gtgcaaggcg   2160
catggccatc ttgggagaca cagcctggga ctttggatca gtgggtggtg ttttgaattc   2220
attagggaaa atggtccacc aaatatttgg gagtgcttac acagccctat ttggtggagt   2280
```

```
ctcctggatg atgaaaattg gaataggtgt cctcttaacc tggatagggt tgaactcaaa    2340
aaatacttct atgtcatttt catgcatcgc gataggaatc attacactct atctgggagc    2400
cgtggtgcaa gctgacatgg ggtgtgtcat aaactggaaa ggcaaagaac tcaaatgtgg    2460
aagtggaatt ttcgtcacta atgaggtcca cacctggaca gagcaataca aatttcaagc    2520
agactccccc aagagactgg caacagccat tgcaggcgct tgggaaaatg gagtgtgcgg    2580
aattaggtca caaccagaa tggagaacct cttgtgaag caaatagcca atgaactgaa     2640
ttacatatta tgggaaaaca acattaaatt aacggtagtt gtaggcgaca taactggggt    2700
cttagagcaa gggaaaagaa cactaacacc acaacccatg gagctaaaat attcttggaa    2760
aacatgggga aaggcaaaaa tagtgacagc tgaaacacaa aattcctctt tcataataga    2820
tgggccaagc acaccggagt gtccaagtgc ctcaagagca tggaatgtgt gggaggtgga    2880
ggattacggg ttcggagttt tcacaaccaa catatggctg aaactccgag aggtgtacac    2940
ccaactatgt gaccataggc taatgtcggc agccgtcaag gatgagaggg ctgtacatgc    3000
cgacatgggc tattggatag aaagccaaaa gaatgggagt tggaagctag aaaaagcatc    3060
cttcatagag gtgaaaacct gcacatggcc aaaatcacac actctctgga gcaatggtgt    3120
gctagagagt gacatgatta tcccaaagag tctagctggt cccatttcgc aacacaacca    3180
caggcccggg taccacaccc aaacggcagg accctggcac ttaggaaaat tggagctgga    3240
cttcaactat tgtgaaggaa caacagttgt catctcagaa aactgtggga caagaggccc    3300
atcattgaga caacaacgg tgtcaggaa gttgatacac gaatggtgct gccgctcgtg     3360
cacacttcct cccctacgat acatgggaga agacggctgc tggtatggca tggaaatcag    3420
acccattaat gagaaagaag agaatatggt aaagtctcta gccctcagcag ggagtggaaa   3480 ggtggacaac ttcacaatgg gtgtcttgtg tttggcaatc ctctttgaag aggtgatgag    3540
aggaaaattt gggaaaaaac acatgattgc aggggttctc ttcacgtttg tgctcctcct    3600
ctcagggcaa ataacatgga gagacatggc gcacacactc ataatgattg gtccaacgc     3660 ctctgacaga atggggatgg gcgtcactta cctagctcta attgcaacat ttaaaattca    3720
gccactcctg gctttgggat tcttcctgag gaaactgaca tctagagaaa atttattgct    3780
gggagttggg ttggccatgg cagcaacgtt acgactgcca gaggacattg aacagatggc    3840
gaatggaatt gctttgggc tcatggctct taaactgata acacaatttg aaacatacca    3900
actatggacg gcattagttt ccctaacgtg ttcaaataca attttcacgt tgactgttgc    3960
ctggagaaca gccactctga ttttagccgg aatttcgctt ttgccagtgt gccagtcttc    4020
gagcatgagg aaaacagatt ggctcccaat gactgtggca gctatgggag ctcaacccct    4080
accacttttt atttttcagtc tgaaagatac actcaaaagg agaagctggc cactgaatga    4140
gggggtgatg gcagttggac ttgtgagcat tctagctagt tctctcctta ggaatgatgt    4200
gcctatggct ggaccattag tggctggggg cttgctgata gcgtgctacg tcataactgg    4260
cacgtcagca gacctcactg tagaaaaagc agcagatgta acatgggagg aagaggccga    4320
gcaaacagga gtgtcccaca tttaatggt cacagttgat gatgatgaa caatgagaat       4380 aaaagatgac gagactgaga acatcttaac agtgcttta aaaacagcac tactaatagt     4440
atcaggcatc tttccatact ccatacccgc aacactgttg gtctggcata cttggcaaaa    4500
gcaaacccaa agatccggcg tcctatggga cgtacccagc cccccagaga cacagaaagc    4560
ggaactggaa gaagggtct ataggatcaa acagcaagga ttttttggga aacccaagt      4620 gggggttgga gtacagaaag aaggagtttt ccacaccatg tggcatgtca caagagggc     4680
```

-continued

```
agtgttgaca cacaatggga aaagactgga accaaactgg gctagcgtga aaaaagatct    4740
gatttcatac ggaggaggat ggagattgag tgcacaatgg aaaaaggggg aggaggtgca    4800
ggttattgcc gtagagcctg gaagaaccc  aaagaactt  caaaccatgc caggcatttt    4860
tcagacaaca acaggggaaa taggagcaat tgcactggat tcaagcctg  aacttcagg    4920
atctcccatc ataaacagag agggaaaggt agtgggactg tatggcaatg gagtggttac    4980
aaagaatgga ggctatgtca gtggaatagc gcaaacaaat gcagaaccag atggaccgac    5040
accagagttg gaagaagaga tgttcaaaaa gcgaaatcta accataatgg atctccatcc    5100
tgggtcagga aagacgcgga aatatcttcc agctattgtt agagaggcaa tcaagagacg    5160
cttaaggact ctaattttgg caccaacaag ggtagttgca gctgagatgg aagaagcatt    5220
gaaagggctc ccaataaggt atcaaacaac tgcaacaaaa tctgaacaca caggaagaga    5280
gattgttgat ctaatgtgtc acgcaacgtt cacaatgcgc ttgctgtcac cagtcagggt    5340
tccaaactac aacttgataa taatggatga ggcccatttc acagaccag  ccagtatagc    5400
ggctagaggg tacatatcaa ctcgtgtagg aatgggagag gcagccgcaa ttttcatgac    5460
agcaacaccc cctggaacag ctgatgcctt tcctcagagc aacgctccaa ttcaagatga    5520
agagagagac ataccggaac gctcatggaa ttcaggcaat gaatggatta ctgactttgt    5580
tgggaagaca gtgtggtttg tccctagcat caaagccgga aatgacatag caaactgctt    5640
gcggaaaaat ggaaaaaagg ttattcaact cagcaggaag acctttgaca cagaatatca    5700
aaagaccaaa ctgaatgatt gggactttgt ggtgacaaca gacatttcag aaatgggagc    5760
caatttcaaa gcagatagag tgatcgaccc aagaagatgt ctcaagccgg tgattttgac    5820
agatggaccc gagcgggtga tcctggctgg accaatgcca gtcaccgtag cgagcgctgc    5880
gcaaaggaga gggagagttg gcaggaaccc acaaaaagaa aatgaccagt acatattcat    5940
gggccagcct ctcaacaatg atgaagacca tgctcactgg acagaagcaa aaatgctgct    6000
ggacaacatc aacacaccag aagggattat accagctctc tttgaaccag aaaagggagaa    6060
gtcagccgcc atagacggcg aataccgcct gaagggtgag tccaggaaga ctttcgtgga    6120
actcatgagg aggggtgacc tcccagtttg gctagcccat aaagtagcat cagaagggat    6180
caaatataca gatagaaaat ggtgctttga tggagaacgt aataatcaaa ttttagagga    6240
gaatatggat gtgaaatct  ggacaaagga aggagaaaag aaaaaactga gacctaggtg    6300
gcttgatgcc cgcacttatt cagatcctt  agcactcaaa gaattcaagg attttgcagc    6360
tggcagaaag tcaatcgccc ttgatcttgt gacagaaata ggaagagtgc ttcacactt    6420
agcccacaga acgagaaacg ccctggataa tttggtgatg ctgcacacgt cagaacatgg    6480
cggtaggcc  tacaggcatg cagtggagga actaccagaa acgatggaaa cactcttact    6540
cctgggactg atgatcttgt taacaggtgg agcaatgctc ttcttgatat caggtaaagg    6600
gattggaaag acttcaatag gactcatttg tgtaattgct tccagcggca tgttatggat    6660
ggctgatgtc ccactccaat ggatcgcatc ggctatagtc ctggagtttt ttatgatggt    6720
gttgctcata ccagaaccag aaaagcagag aactcccca  gacaaccaac tcgcatatgt    6780
cgtgataggc atacttacat tggctgcaat agtagcggcc aatgaaatgg gactgttgga    6840
aactacaaag agagatttag gaatgtctaa agaaccaggt gttgtttctc caaccagcta    6900
tttggatgtg gacttgcacc cagcatcagc ctggacattg tacgccgtgg ccacaacagt    6960
aataacacca atgttgagac acaccataga gaattccaca gcaaatgtgt ctctggcagc    7020
catagctaac caggcagtgg tcctgatggg tttagacaaa ggatggccga tatcgaaaat    7080
```

```
ggacttgggc gtaccactat tggcactggg ttgctattca caagtgaacc cactaactct    7140
tgcagcggca gtacttttgc tagtcacaca ttatgcaatt ataggtccag gattgcaggc    7200
aaaagccacc cgtgaagctc agaaaaggac agctgctgga ataatgaaga atccaacggt    7260
ggatggaata atgacaatag acctagatcc tgtaatatat gattcaaaat ttgaaaagca    7320
actaggacag gtcatgctcc tggttctgtg tgcagtccaa cttttattga tgagaacatc    7380
atgggccttg tgtgaagttc taaccctagc cacaggacca ataacaacac tctgggaagg    7440
atcacctggg aagttctgga acaccacgat agctgtttcc atggcgaaca tctttagagg    7500
gagctattta gcaggagctg ggcttgcttt ttctatcatg aaatcagttg gaacaggaaa    7560
gagaggaaca gggtcacaag gtgaaacctt aggagaaaag tggaaaaaga aattaaatca    7620
gttatcccgg aaagagtttg acctttacaa gaaatccgga atcaccgaag tggatagaac    7680
agaagccaaa gaagggttaa aaagaggaga ataacacac catgccgtgt ccagaggcag    7740
cgcaaaactt caatggttcg tgagagaaa catggtcatt cctgaaggaa gagtcataga    7800
cctaggctgt ggaagaggag gctggtcata ttactgtgca ggactgaaaa aagttacaga    7860
agtgcgagga tacacaaaag gcggcccagg acacgaagaa ccagtaccta tgtctacata    7920
cggatggaac atagtcaagt taatgagtgg aaaggatgtt ttttatctgc cacctgaaaa    7980
gtgtgatacc ctattgtgtg acattggaga atcttcacca agcccaacag tggaagaaag    8040
cagaaccata agagttttga agatggttga accatggcta agaacaacc agttttgcat    8100 taaagtattg aacccataca tgccaactgt gattgagcac ttagaaagac tacaaaggaa    8160
acatggagga atgcttgtga gaaatccact ctcacgaaac tccacgcacg aaatgtattg    8220
gatatccaat ggtacaggca atatcgtctc ttcagtcaac atggtatcca gattgctact    8280
gaacagattc acaatgacac acaggagacc caccatagag aaagatgtgg atctaggagc    8340
aggaacccga catgtcaatg cggaaccaga aacacccaac atggatgtca ttggggaaag    8400
aataaaaagg atcaaagagg agcatagttc aacatggcac tatgatgatg aaaatcctta    8460
caaaacgtgg gcttaccatg gatcctatga agtaaaagcc acaggctcag cctcctccat    8520
gataaatgga gtcgtgaaac tcctcacaaa accatgggat gtggtgccca tggtgacaca    8580
gatggcaatg acagatacaa ctccattcgg ccagcaaaga gtttttaaag agaaagtgga    8640
caccaggaca cctaggccca tgccaggaac aagaaaggtt atgagatca cagcggagtg    8700 gctttggagg acctgggaa ggaacaaaag acccagatta tgcacaaggg aggaattcac    8760
aaagaaggtc agaaccaacg cagctatggg cgctgtcttc acagaagaga accaatggga    8820
cagtgcgaga gctgctgttg aggacgaaga attttggaaa cttgtggaca gagaacgtga    8880
actccacaaa ctgggcaagt gtggaagctg cgtttacaac atgatgggca agagagaaaa    8940
aaaacttgga gagtttggta agcaaaagg cagtagggct atatggtaca tgtggttggg    9000
agccaggtac cttgagttcg aggcgctcgg attcctcaat gaagaccact ggttctcgcg    9060
tgaaaactct acagtggag tagaaggaga aggactgcac aagctgggat acatcttgag    9120
agatatttcc aagatcccg gaggagccat gtatgctgat gacacagccg ttgggacac    9180 aagaataaca gaagatgacc tgcacaatga ggaaaaaatc acacagcaga tggaccctga    9240
acacaggcag ctagcgaacg ctatattcaa gctcacatac caaaacaaag tggtcaaagt    9300
ccaacgacca actccaaagg gcacggtaat ggacatcata tctaggaaag accaaaagagg    9360 cagtggacag gtgggaactt atggtctgaa cacattcacc aacatggaag cccagctaat    9420
cagacaaatg gaaggagaag gcgtgttgtc aaaggcagac ctcgagaacc cccatccgct    9480
```

| | |
|---|---:|
| agagaagaaa attacacaat ggttggaaac taaaggagtg gaaaggttaa aaagaatggc | 9540 |
| catcagcggg gatgattgcg ttgtgaaacc aatcgacgac agattcgcca atgccctgct | 9600 |
| tgccctgaac gatatgggaa aggttagaaa ggacatacct caatggcagc catcaaaggg | 9660 |
| atggcatgat tggcaacagg tccccttctg ctcccaccac tttcatgaat tgatcatgaa | 9720 |
| agatggaaga agttggtag ttccctgcag accccaggac gaactaatag gaagagcgag | 9780 |
| aatctcccaa ggagcaggat ggagccttag agaaactgca tgtctaggga aagcctacgc | 9840 |
| tcaaatgtgg gctctcatgt atttttcacag aagagatctt agactagcat ccaacgccat | 9900 |
| atgttcagca gtaccagtcc actgggtccc cacgagcaga acgacatggt ctattcatgc | 9960 |
| tcaccatcag tggatgacta cagaagacat gcttactgtc tggaacaggg tgtggataga | 10020 |
| ggacaatcca tggatggaag acaaaactcc agtcacaacg tgggaagatg ttccatatct | 10080 |
| agggaagaga gaagaccaat ggtgcggatc actcataggt ctcacttcca gagcaacctg | 10140 |
| ggcccagaac atactcacag caatccaaca ggtgagaagc ctcataggca atgaagagtt | 10200 |
| tctggactac atgccttcga tgaagagatt caggaaggag gaggagtcag agggagccat | 10260 |
| ttggtaaaag caggaggtaa actgtcaggc cacattaagc cacagtacgg aagaagctgt | 10320 |
| gcagcctgtg agccccgtcc aaggacgtta aaagaagaag tcaggcccaa aagccacggt | 10380 |
| ttgagcaaac cgtgctgcct gtagctccgt cgtggggacg taaagcctgg gaggctgcaa | 10440 |
| accgtggaag ctgtacgcac ggtgtagcag actagtggtt agaggagacc cctcccatga | 10500 |
| cacaacgcag cagcggggcc cgagcactga gggaagctgt acctccttgc aaaggactag | 10560 |
| aggttagagg agaccccccg caaacaaaaa cagcatattg acgctgggag agaccagaga | 10620 |
| tcctgctgtc tcctcagcat cattccaggc acagaacgcc agaaaatgga atggtgctgt | 10680 |
| tgaatcaaca ggttctagt | 10699 |

<210> SEQ ID NO 12
<211> LENGTH: 10648
<212> TYPE: DNA
<213> ORGANISM: Dengue virus type 4 (LAV4)

<400> SEQUENCE: 12

| | |
|---|---:|
| agttgttagt ctgtgtggac cgacaaggac agttccaaat cggaagcttg cttaacacag | 60 |
| ttctaacagt ttgtttgaat agagagcaga tctctggaaa aatgaaccaa cgaaaaaagg | 120 |
| tggttagacc acctttcaat atgctgaaac gcgagagaaa ccgcgtatca ccccctcaag | 180 |
| ggttggtgaa gagattctca accggacttt tttctgggaa aggaccctta cggatggtgc | 240 |
| tagcattcat cacgttttg cgagtccttt ccatcccacc aacagcaggg attctgaaaa | 300 |
| gatggggaca gttgaagaaa ataaggccat caggatact gattggattc aggaaggaga | 360 |
| taggccgcat gctgaacatc ttgaacggga gaaaaggtc aacgataaca ttgctgtgct | 420 |
| tgattcccac cgtaatggcg tttcacttgt caacaagaga tggcgaaccc tcatgatag | 480 |
| tggcaaaaca tgaaaggggg agacctctct tgtttaagac aacagagggg atcaacaaat | 540 |
| gcactctcat tgccatggac ttgggtgaaa tgtgtgagga cactgtcacg tataaatgcc | 600 |
| ccttactggt caataccgaa cctgaagaca ttgattgctg gtgcaatctc acgtctacct | 660 |
| gggtcatgta tgggacatgc acccagagcg agaacggag acgagagaag cgctcagtag | 720 |
| ctttaacacc acattcagga atgggattgg aaacaagagc tgagacatgg atgtcatcgg | 780 |
| aaggggcttg gaagcatgct cagagagtag agagctggat actcagaaac ccaggattcg | 840 |
| cgctcttggc aggatttatg gcttatatga ttgggcaaac aggaatccag cgaactgtct | 900 |

```
tctttgtcct aatgatgctg gtcgccccat cctacggaat gcgatgcgta ggagtaggaa      960
acagagactt tgtggaagga gtctcaggtg gagcatgggc cgatctggtg ctagaacatg     1020
gaggatgcgt cacaaccatg gcccagggaa aaccaacctt ggattttgaa ctgactaaga     1080
caacagccaa ggaagtggct ctgttaagaa cctattgcat tgaagcctca atatcaaaca     1140
taaccacggc aacaagatgt ccaacgcaag gagagcctta tctaaaagag gaacaagacc     1200
aacagtacat ctgccggaga gatgtggtag acagagggtg gggcaatggc tgtggcttgt     1260
ttggaaaagg aggagttgtg acatgtgcga agttttcatg ttcggggaag ataacaggca     1320
atttggtcca aattgagaac cttgaataca cagtggttgt aacagtccac aatggagaca     1380
cccatgcagt aggaaatgac acatccaatc atggagttac agccacgata actcccaggt     1440
caccatcggt ggaagtcaaa ttgccggact atggagaact aacactcgat tgtgaaccca     1500
ggtctggaat tgactttaat gagatgattc tgatgaaaat gaaaagaaa acatggcttg     1560 tgcataagca atggttttg gatctacctc taccatggac agcaggagca gacacatcag     1620
aggttcactg gaattacaaa gagagaatgg tgacatttaa ggttcctcat gccaagagac     1680
aggatgtgac agtgctggga tctcaggaag gagccatgca ttctgccctc gctggagcca     1740
cagaagtgga ctccggtgat ggaaatcaca tgtttgcagg acatctcaag tgcaaagtcc     1800
gtatggagaa attgagaatc aagggaatgt catacacgat gtgttcagga aagttctcaa     1860
ttgacaaaga gatggcagaa acacagcatg gacaacagt ggtgaaagtc aagtatgaag     1920
gtgctggagc tccgtgtaaa gtccccatag agataagaga tgtgaacaag aaaaagtgg     1980 ttgggcgtat catctcatcc acccctttgg ctgagaatac caacagtgca accaacatag     2040
agttagaacc ccccttgggg gacagctaca gtgatagg tgttggaaac agtgcattaa      2100
cactccattg gttcaggaaa gggagttcca ttggcaagat gtttgagtcc acatacagag     2160
gtgcaaaacg aatggccatt ctaggtgaaa cagcttggga ttttggttcc gttggtggac     2220
tgttcacatc attgggaaag gctgtgcacc aggttttgg aagtgtgtat acaaccatgt     2280
ttggaggagt ctcatggatg attagaatcc taattgggtt cctagtgttg tggattggca     2340
cgaactcaag gaacacttca atggctatga cgtgcatagc tgttggagga atcactctgt     2400
ttctgggctt cacagttcaa gcagacatgg gttgtgtggt gtcatggagt gggaaagaat     2460
tgaagtgtgg aagcggaatt tttgtggttg acaacgtgca cacttggaca gaacagtaca     2520
aatttcaacc ggagtcccca gcgagactag cgtctgcaat attgaatgcc cacaaagatg     2580
gggtctgtgg aattagatca accacgaggc tggaaaatgt catgtggaag caaataacca     2640
acgagctaaa ttatgttctc tgggaaggag acatgacct cactgtagtg gctggggatg     2700 tgaaggggg gttgaccaaa ggcaagagag cactcacacc cccagtgaat gatctgaaat     2760
attcatggaa gacatgggga aaagcaaaaa tcttcacccc agaagcaaga aatagcacat     2820
ttttaataga cggaccagac acctccgaat gccccaatga acgaagagca tggaactttc     2880
ttgaggtgga agactatgga tttggcatgt tcacgaccaa catatggatg aaattccgag     2940
aaggaagttc agaagtgtgt gaccacaggt taatgtcagc ggcaattaaa gatcagaaag     3000
ctgtgcatgc tgacatgggt tattggatag agagctcaaa aaccagacc tggcagatag     3060 agaaagcatc tctattgaa gtgaaaacat gtctgtggcc caagacccac acattgtgga     3120
gcaatggagt gctggaaagc cagatgctca ttccaaaatc atatgcgggc cctttttcac     3180
accacaatta ccgccagggc tatgccacgc aaaccgtggg cccatggcac ttaggcaaat     3240
tagagataga ctttggagaa tgccccggaa caacagtcgc aattcaggag gattgtgacc     3300
```

```
atagaggccc atctttgagg accaccactg catctggaaa actagtcacg caatggtgct    3360
gccgctcctg cacgatgcct cccttaaggt tcttgggaga agatgggtgc tggtatggga    3420
tggagattag gcccttgagt gaaaagaag agaacatggt caaatcacag gtaacggccg     3480
gacagggcac atcagaaact ttttctatgg gtctgttgtg cctgaccttg tttgtggaag    3540
aatgcttgag gagaagagtc actaggaaac acatgatatt ggttgtggtg atcactcttt    3600
gtgccatcat cctaggaggc ctcacatgga tggacttact acgagccctc atcatgttgg    3660
gggacactat gtctggtaga ataggaggac agatccacct agccatcatg gcagtgttca    3720
agatgtcacc aggatacgtg ctgggtgtgt ttttaaggaa actcacttca agagagacag    3780
cactaatggt aataggaatg gccatgacaa cggtgctttc aattccacat gaccttatgg    3840
aactcattga tggaatatca ctggggctaa ttttgctaaa aatagtgaca cattttgaca    3900
acacccaagt gggaaccttag gccctttcct tgaccttcat aagatcaaca atgccattgg    3960
tcatggcttg gaggaccatt atggctgtgt gtttgtggt cacactcatt cctttgtgca     4020
ggacaagctg tcttcaaaaa cagtctcatt gggtagaaat aacagcactc atcctaggag    4080
cccaagctct gccagtgtac ctaatgactc ttatgaaagg agcctcaaga agatcttggc    4140
ctcttaacga gggcataatg gctgtgggtt tggttagtct cttaggaagc gctcttttaa    4200
agaatgatgt ccctttagct ggcccaatgg tggcaggagg cttacttctg gcggcttacg    4260
tgatgagtgg tagctcagca gatctgtcac tagagaaggc cgccaatgtg cagtgggatg    4320
aaatggcaga cataacaggc tcaagcccaa tcatagaagt gaagcaggat gaagatggct    4380
cttttctccat acgggacgtc gaggaaacca atatgataac ccttttggtg aaactggcac    4440
tgataacagt gtcaggtctc tacccccttgg caattccagt cacaatgacc ttatggtaca    4500
tgtggcaagt gaaaacacaa agatcaggag ccctgtggga cgtcccctca cccgctgcca    4560
ctcaaaaagc cgcactgtct gaaggagtgt acaggatcat gcaaagaggg ttatttggga    4620
aaactcaggt tggagtaggg atacacatgg aaggtgtatt tcacacaatg tggcatgtaa    4680
caagaggatc agtgatctgc catgagactg ggagattgga gccatcttgg gctgacgtca    4740
ggaatgacat gatatcatac ggtgggggat ggagacttgg agacaaatgg gacaaagaag    4800
aagatgttca ggtcctcgcc atagaaccag gaaaaaatcc taaacatgtc caaacgaaac    4860
ccggcctttt caagaccccta actggagaaa ttggagcagt aacattagat ttcaaacccg    4920
gaacgtctgg ttctcccatc atcaacagga aggaaaagt catcggactc tatggaaatg     4980
gagtagttac caaatcaggt gattacgtca gtgccataac gcaagccgaa agaattggag    5040
agccagatta tgaagtggat gaggacattt ttcgaaagaa aagattaact ataatggact    5100
tacaccccgg agctggaaag acaaaaagaa ttcttccatc aatagtgaga gaagccttaa    5160
aaaggaggct gcgaaccttg attttggctc ccacgagagt ggtggcggcc gagatggaag    5220
aggcccctacg tggactgcca atccgttatc agacccccagc tgtgaaatca gaacacacg    5280
gaagagagat tgtagacctc atgtgtcatg caaccttcac aacaagactt ttgtcatcaa    5340
ccagagttcc aaattacaac ctcatagtga tggatgaagc acatttcacc gatccttcta    5400
gtgtcgcggc tagaggatac atctcgacca gggtggaaat gggagaggca gcagccatct    5460
tcatgaccgc aacccctccc ggagcgcagc atcccttttcc ccagagcaac agcccaatag    5520
aagacatcga gagggaaatt ccggaaaggt catggaacac agggttcgac tggataacag    5580
actaccaagg gaaaactgtg tggttttgtt ccagcataaa agctgaaat gacattgcaa     5640
attgttttga aagtcggga aagaaagtta tccagttgag taggaaaacc tttgatacag    5700
```

```
agtatccaaa aacgaaactc acggactggg attttgtggt cactacagac atatctgaaa   5760
tgggggccaa ttttagagct gggagagtga tagaccctag gagatgcctc aagccagtta   5820
tcctaacaga tgggccagag agagtcattt tagcaggtcc tattccagtg actccagcaa   5880
gcgctgctca gagaagaggg cgaataggaa ggaacccagc acaagaagac gaccaatacg   5940
ttttctccgg agacccacta aaaatgatg aagatcatgc ccactggaca gaagcaaaga   6000
tgctgcttga caatatctac accccagaag ggatcattcc aacattgttt ggtccggaaa   6060
gggaaaaaac ccaagccatt gatggagagt ttcgcctcag aggggaacaa aggaagactt   6120
ttgtggaatt aatgaggaga ggagaccttc cggtgtggct gagctataag gtagcttctg   6180
ctggcatttc ttacaaagat cgggaatggt gcttcacagg ggaaaggaat aaccaaattt   6240
tagaagaaaa catggaggtt gaaatttgga ctagagaggg agaaaagaaa aagctaaggc   6300
caagatggtt agatgcacgt gtatacgctg accccatggc tttgaaggat tttaaggagt   6360
ttgctagtgg aaggaagagc ataactctcg acatcctaac agagattgcc agtttgccaa   6420
cttacctttc ctctagggcc aagctcgccc ttgataacat agtcatgctc cacacaacag   6480
aaagaggagg gagggcctac caacacgccc tgaacgaact cccggagtca ctggaaacac   6540
ttatgcttgt agctttacta ggtgctatga cagcaggtat cttcctgttt ttcatgcaag   6600
ggaaaggaat agggaaattg tcaatgggtt tgataaccat tgcggtggct agtggcttgt   6660
tctgggtagc agaaattcaa ccccagtgga tagcggcctc aatcatacta gagttttttc   6720
tcatggtact gttgataccg gaaccagaaa acaaaggac cccacaagac aatcaattga   6780
tctacgtcat attgaccatt ctcaccatta ttggtctcat agcagccaac gagatggggc   6840
tgattgaaaa aacaaaaacg attttgggt tttaccaggt aaaaacagaa accaccatcc   6900
tcgatgtgga cttgagacca gcttcagcat ggacgctcta tgcagtagcc accacawttc   6960
tgactcccat gctgagacac accatagaaa acacgtcggc caacctatct ctagcagcca   7020
ttgccaacca ggcggccgtc ctaatggggc ttggaaaagg atggccgctc cacagaatgg   7080
acctcggtgt gccgctgtta gcaatgggat gctattctca gtgaaccca caactttga   7140
cagcatcctt agtcatgctt tcagtccatt atgcaataat aggtccagga ttgcaggca   7200
aagccacaag agaggcccag aaaaggacag ctgctgggat catgaaaaac cccacggtgg   7260
acgggataac agtaatagat ctagaaccaa tatcctatga cccaaaattt gaaaagcaat   7320
tagggcaggt catgctactc gtcttgtgtg ctggacaact actcttgatg agaacaacat   7380
gggcttctctg tgaagtcttg actttggcca caggaccaat cttgaccttg tggggaggca   7440
acccgggaag gttttggaac acgaccatag ccgtatccac cgccaacatt tcaggggaa   7500
gttacctggc gggagctgga ctggcttttt cactcataaa gaatgyacaa accccctagga   7560
ggggaactgg gaccacagga gagacactgg gagagaagtg aagagacag ctaaactcat   7620
takacagaaa agagtttgaa gagtatataaa gaagtggaat actagaagtg gacaggactg   7680
aagccaagtc tgccctgaaa gatgggtcta aaatcaagca tgcagtatct agagggtcca   7740
gtaagattag atggattgtt gagagaggga tggtaaagcc aaaagggaaa gttgtagatc   7800
ttggctgtgg gagaggagga tggtcttatt acatggcgac gctcaagaac gtgactgaag   7860
tgaaaggta tacaaaagga ggtccaggac atgaagaacc gattcccatg gctacttatg   7920
gctggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
```

-continued

```
tcaaagtcct taacccctac atgccaacag tcatagaaga gctggagaaa ctgcagagaa    8160
aacatggtgg gaaccttgtc agatgcccgc tgtccaggaa ctccacccat gagatgtatt    8220
gggtgtcagg agcgtcggga acattgtga gctctgtgaa cacaacatca aagatgttgt    8280
tgaacaggtt cacaacaagg cataggaaac ccacttatga aaggacgta gatcttgggg    8340
caggaacgag aagtgtctcc actgaaacag aaaaaccaga catgacaatt attgggagaa    8400
ggcttcagcg attgcaagag gagcacaaag aaacctggca ttatgatcag gaaacccat    8460
acagaacctg gccgtatcat ggaagctatg aagctccttc gacaggctct gcatcctcca    8520
tggtgaacgg ggtagtaaaa ctgctaacaa aaccttggga tgtggttcca atggtgaccc    8580
agttagccat gacagacaca accccttttg gcaacaaag agtgttcaaa gagaaggtgg    8640
ataccagaac accacaacca aaacccggta cacgaatggt tatgaccacg acagccaatt    8700
ggctgtgggc cctccttggg aagaagaaaa atcccagact gtgcacaagg aagagttca    8760
tctcaaaagt tagatcaaac gcagccatag gcgcagtctt tcaggaagaa cagggatgga    8820
catcagccag tgaagctgtg aatgacagcc ggttttggga actggttgac aaagaaaggg    8880
ccctacacca ggaagggaaa tgtgaatcgt gtgtctacaa catgatggga aaacgtgaga    8940
aaaagttagg agagtttggc agagccaagg gaagccgagc aatctggtac atgtggctgg    9000
gagcgcggtt tctggaattt gaagccctgg ttttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aagaactgat cacggaacag atggcccccc    9240
accacaagat cctagccaaa gccatttca aactaaccta tcaaaacaaa gtggtgaaag    9300
tcctcagacc cacaccgaga ggagcggtga tggatatcat atccaggaaa gaccaaagag    9360
gtagtggaca agttggaaca tatggtttga acacattcac caacatggaa gttcaactca    9420
tccgccaaat ggaagctgaa ggagtcatca cacaagatga catgcagaac ccaaaagggt    9480
tgaaagaaag agttgagaaa tggctgaaag agtgtggtgt cgacaggtta aagaggatgg    9540
caatcagtgg agacgattgc gtggtgaagc ccctggatga gaggtttggc acttccctcc    9600
tcttcttgaa cgacatggga aaggtgagga agacattcc gcagtgggaa ccatctaagg    9660
gatgaaaaa ctggcaagag gttcctttt gctcccacca ctttcacaag atcttcatga    9720
aggatggccg ctcactagtt gttccatgta gaaaccagga tgaactgata gggagagcca    9780
gaatctcgca gggggctgga tggagcttaa gagaaacagc ctgcctgggc aaagcttacg    9840
cccagatgtg gtcgctcatg tacttccaca aagggatct gcgtttagcc tccatggcca    9900
tatgctcagc agttccaacg gaatggtttc caacaagcag aacaacatgg tcaatccacg    9960
ctcatcatca gtggatgacc actgaagata tgctcaaagt gtggaacaga gtgtggatag   10020
aagacaaccc taatatgact gacaagactc cagtccattc gtgggaagat ataccttacc   10080
tagggaaaag agaggatttg tggtgtggat ccctgattgg actttcttcc agagccacct   10140
gggcgaagaa cattcacacg gccataaccc aggtcagaaa cctgatcgga aaagaggaat   10200
acgtggatta catgccagta atgaaaagat acagcgctcc ttcagagagt gaaggagttc   10260
tgtaattacc aacaacaaac accaaggct attgaagtca ggccacttgt gccacggctt   10320
gagcaaaccg tgctgcctgt agctccgcca ataatgggag gcgtgaaatc cctagggagg   10380
ccatgcgcca cggaagctgt acgcgtggca tattggacta gcggttagag gagacccctc   10440
ccatcactga caaaacgcag caaaggggg cccgaagcca ggaggaagct gtactcctgg   10500
```

```
tggaaggact agaggttaga ggagacccccc ccaacacaaa aacagcatat tgacgctggg    10560
aaagaccaga gatcctgctg tctctgcaac atcaatccag gcacagagcg aagcaagatg    10620
gattggtgtt gttgatccaa caggttct                                       10648
```

<210> SEQ ID NO 13
<211> LENGTH: 10735
<212> TYPE: DNA
<213> ORGANISM: Dengue virus VDV1

<400> SEQUENCE: 13

```
agttgttagt ctacgtggac cgacaagaac agtttcgaat cggaagcttg cttaacgtag      60
ttctaacagt tttttattag agagcagatc tctgatgatc aaccaacgaa aaaagacggg     120
tcgaccgtct ttcaatatgc tgaaacgcgc gagaaaccgc gtgtcaactg tttcacagtt     180
ggcgaagaga ttctcaaaag gattgctctc aggccaagga cccatgaaat tggtgatggc     240
tttcatagca ttcttaagat ttctagccat accccccaaca gcaggaattt tggctagatg     300
gggctcattc aagaagaatg gagcgattaa agtgttacgg ggtttcaaga gagaaatctc     360
aaacatgcta aacataatga acaggaggaa aagatccgtg accatgctcc ttatgctgct     420
gcccacagcc ctggcgttcc atctgacgac acgagggggga gagccgcata tgatagttag     480
caagcaggaa agaggaaagt cacttttgtt caagacctct gcaggtgtca acatgtgcac     540
cctcattgcg atggatttgg gagagttgtg tgaggacacg atgacctaca atgcccccg      600 gatcactgag gcggaaccag atgacgttga ctgttggtgc aatgccacgg acacatgggt     660
gacctatgga acgtgctctc aaactggcga acaccgacga gacaaacgtt ccgtcgcatt     720 ggcccccacac gtgggggcttg gcctagaaac aagagccgaa acgtggatgt cctctgaagg     780
tgcttggaaa cagatacaaa aagtagagac ttgggctctg agacatccag gattcacggt     840 gatagcccctt tttctagcac atgccatagg aacatccatc acccagaaag ggatcatttt     900 catttttgctg atgctggtaa caccatctat ggccatgcga tgcgtgggaa taggcaacag     960
agacttcgtg gaaggactgt caggagcaac atgggtggat gtggtactgg agcatggaag    1020
ttgcgtcacc accatggcaa aaaacaaacc aacactggac attgaactct tgaagacgga    1080
ggtcacaaac cctgcagttc tgcgtaaatt gtgcattgaa gctaaaatat caaacaccac    1140
caccgattcg agatgtccaa cacaaggaga agccacactg gtggaagaac aagacgcgaa    1200
ctttgtgtgc cgacgaacgt tcgtggacag aggctggggc aatggctgtg ggctattcgg    1260
aaaaggtagt ctaataacgt gtgccaagtt taagtgtgtg acaaaactag aaggaaagat    1320
agctcaatat gaaaaaccta aatattcagt gatagtcacc gtccacactg gagatcagca    1380
ccaggtggga aatgagacta cagaacatgg aacaactgca accataacac ctcaagctcc    1440
tacgtcggaa atacagctga ccgactacgg aaccccttaca ttagattgtt cacctaggac    1500
agggctagat tttaacgaga tggtgttgct gacaatgaaa aagaaatcat ggcttgtcca    1560
caaacagtgg tttctagact accactgcc ttggacctct ggggctttaa catcccaaga    1620
gacttggaac agacaagatt tactggtcac atttaagaca gctcatgcaa agaagcagga    1680
agtagtcgta ctaggatcac aagaaggagc aatgcacact gcgctgactg gagcgacaga    1740
aatccaaacg tcaggaacga caacaatttt cgcaggacac ctaaaatgca gactaaaaat    1800
ggacaaacta actttaaaag ggatgtcata tgtgatgtgc acaggctcat tcaagttaga    1860
gaaagaagtg gctgagaccc agcatggaac tgttctggtg caggttaaat atgaaggaac    1920
agacgcacca tgcaagattc ccttttcgac ccaagatgag aaaggagcaa cccagaatgg    1980
```

```
gagattaata acagccaacc ccatagtcac tgacaaagaa aaaccagtca atattgaggc    2040
agaaccaccc tttggtgaga gctacatcgt ggtaggagca ggtgaaaaag ctttgaaact    2100
aagctggttc aagaaaggaa gcagcatagg gaaaatgttt gaagcaactg cccgaggagc    2160
acgaaggatg gccattctgg gagacaccgc atgggacttc ggttctatag gaggagtgtt    2220
cacgtctatg ggaaaactgg tacaccaggt ttttggaact gcatatggag ttttgtttag    2280
cggagtttct tggaccatga aaataggaat agggattctg ctgacatggc taggattaaa    2340
ttcaaggaac acgtcccttt cggtgatgtg catcgcagtt ggcatggtca cactgtacct    2400
aggagtcatg gttcaggcag attcgggatg tgtaatcaac tggaaaggca gagaacttaa    2460
atgtggaagc ggcattttg tcactaatga agttcacact tggacagagc aatacaaatt    2520
ccaggctgac tccccaaga gactatcagc agccattggg aaggcatggg aggagggtgt    2580
gtgtggaatc cgatcagcca ctcgtctcga gaacatcatg tggaaacaaa tatcaaatga    2640
attgaaccac atcctacttg aaaatgacat gaaatttaca gtggtcgtgg agacgttag    2700
tggaatcttg gcccaaggra aaaaaatgat taggccacaa cccatggaac acaaatactc    2760
gtggaaaagc tggggaaaag ctaaaatcat aggagcggat gtacagaaca ccaccttcat    2820
catcgacggc ccaaacaccc cagaatgccc tgacaatcaa agagcatgga atatttggga    2880
agtagaggac tatggatttg ggattttcac gacaaacata tggttgaaat tgcgtgactc    2940
ctacacccaa gtatgtgacc accggctgat gtcagctgcc attaaggaca gcaaggcagt    3000
ccatgctgac atggggtact ggatagaaag tgaaaagaac gagacatgga gttggcgag    3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag gcaagttgga    3240
actagatttc gattttgtg aaggtaccac agttgttgtg gatgaacatt gtggaaatcg    3300
aggaccatct ctcagaacca caacagtcac aggaaagata atccatgaat ggtgctgcag    3360
atcttgtacg ctaccccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga cactggctg tgttcctcct    3600
tcttataatg ggacaattga catggagtga tctgatcagg ttatgtatta tggttggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta aacagaaaaa caaaatctgg ggaaggaaga gttggccct    4140
caatgaagga attatggctg ttggaatagt tagtattcta ctaagttcac ttttaaaaaa    4200
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
```

```
gaagataaaa gatgaagaga gagatgacac gctcaccatt ctccttaaag caactctgct    4440
ggcagtctca ggggtgtacc caatgtcaat accagcgacc cttttttgtgt ggtattttttg   4500
gcagaaaaag aaacagagat caggagtgct atgggacaca cccagccccc cagaagtgga    4560
aagagcagtt cttgatgatg gcatctatag aattttgcaa agaggactgt tgggcaggtc    4620
ccaagtagga gtaggagttt tccaagaagg cgtgttccac acaatgtggc acgtcactag    4680
gggagctgtc ctcatgtatc aaggaaaaag gctggaacca agctgggcca gtgtcaaaaa    4740
agacttgatc tcatatggag gaggttggag gtttcaagga tcctggaaca cgggagaaga    4800
agtacaggtg attgctgttg aaccgggaaa aaaccccaaa aatgtacaaa caacgccggg    4860
taccttcaag accccctgaag gcgaagttgg agccatagcc ttagacttta aacctggcac    4920
atctggatct cccatcgtaa acagagaggg aaaaatagta ggtctttatg gaaatggagt    4980
ggtgacaaca agcggaactt acgttagtgc catagctcaa gctaaggcat cacaagaagg    5040
gcctctacca gagattgagg acaaggtgtt taggaaaaga aacttaacaa taatggacct    5100
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
tatgacagcc actcccccag gatcggtgga ggcctttcca cagagcaatg caattatcca    5520
agatgaggaa agagacattc ctgagagatc atggaactca ggctatgact ggatcactga    5580
ttttccaggt aaaacagtct ggtttgttcc aagcatcaaa tcaggaaatg acattgccaa    5640
ctgtttaaga aaaacggga aacgggtgat ccaattgagc agaaaaacct ttgacactga    5700
gtaccagaaa acaaaaaaca acgactggga ctatgtcgtc acaacagaca tttccgaaat    5760
gggagcaaat ttccgggccg acagggtaat agacccaagg cggtgtctga accggtaat    5820
actaaaagat ggtccagagc gcgtcattct agccggaccg atgccagtga ctgtggccag    5880
tgccgcccag aggagaggaa gaattggaag gaaccaaaac aaggaaggtg atcagtatat    5940
ttacatggga cagcccttta aaaatgatga ggaccacgct cattggacag aagcaaagat    6000
gctccttgac aatataaaca caccagaagg gattatccca gccctctttg agccggagag    6060
agaaaagagt gcagctatag acggggaata cagactgcgg ggtgaagcaa ggaaaacgtt    6120
cgtggagctc atgagaagag gggatctacc agtctggcta tcctacaaag ttgcctcaga    6180
aggcttccag tactccgaca gaaggtggtg cttcgatggg gaaaggaaca accaggtgtt    6240
ggaggagaac atggacgtgg agatctggac aaaagaagga gaaagaaaga aactacgacc    6300
tcgctggttg gacgccagaa catactctga cccactggct ctgcgcgagt ttaaagagtt    6360
tgcagcagga agaagaagcg tctcaggtga cctaatatta gaaatagggga aacttccaca    6420
acatttgacg caaagggccc agaatgcttt ggacaacttg gtcatgttgc acaattccga    6480
acaaggagga aaagcctata gacatgctat ggaagaactg ccagacacaa tagaaacgtt    6540
gatgctccta gccttgatag ctgtgttgac tggtggagtg acgctgttct tcctatcagg    6600
aagaggtcta ggaaaaacat ctatcggctt actctgcgtg atggcctcaa gcgcactgtt    6660
atggatggcc agtgtggagc cccattggat agcggcctcc atcatactgg agttctttct    6720
gatggtactg cttattccag agccagacag acagcgcact ccacaggaca accagctagc    6780
```

```
atatgtggtg ataggtctgt tattcgtgat attgacagtg gcagccaatg agatgggatt    6840
attggaaacc acaaagaaag acctggggat tggccatgta gctgctgaaa accaccacca    6900
tgctacaatg ctggacgtag acctacatcc agcttcagcc tggaccctct atgcagtggc    6960
cacaacaatc atcactccta tgatgagaca cacaattgaa aacacaacgg caaatatttc    7020
cctgacagcc atcgcaaacc aagcagctat attgatggga cttgacaagg gatggccaat    7080
atcgaagatg gacataggag ttccacttct cgccttgggg tgctattccc aagtgaatcc    7140
gctgacactg atagcggcag tattgatgct agtagctcat tacgccataa ttggacctgg    7200
actgcaagca aaagctacta gagaagctca aaaaagaaca gcggctggaa taatgaaaaa    7260
tccaactgtc gacgggattg ttgcaataga cttagatccc gtggtttacg atgcaaaatt    7320
tgaaaaacag ctaggccaaa taatgttgtt gatactttgc acatcacaga ttcttttgat    7380
gcggactaca tgggccttgt gtgaatccat cacattggct actggacctc tgaccactct    7440
ttgggaggga tctccaggaa aattctggaa caccacaata gcggtatcca tggcaaacat    7500
tttcaggggg agttatctag caggagcagg tctggccttc tcattaatga aatctctagg    7560
aggaggtagg agaggcacgg gagcccaagg ggaaacactg ggagaaaaat ggaaaagaca    7620
actaaaccaa ctgagcaagt cagaattcaa tacttacaag aggagtggga ttatggaggt    7680
ggatagatcc gaagccaaag agggactgaa aagaggagaa acaaccaaac acgcagtatc    7740
gagaggaacg gccaaactga ggtggttcgt ggagaggaac cttgtgaaac agaagggaa     7800
agtcatagac ctcggttgtg aagaggtgg ctggtcatat tattgcgctg ggctgaagaa     7860
agtcacagaa gtgaaaggat acacaaaagg aggacctgga catgaggaac caatcccaat    7920
ggcgacctat ggatggaacc tagtaaggct gcactccgga aaagatgtat tttttatacc    7980
acctgagaaa tgtgacaccc ttttgtgtga tattggtgag tcctctccga acccaactat    8040
agaggaagga agaacgttac gtgttctgaa aatggtggaa ccatggctca gaggaaacca    8100
attttgcata aaaattctaa atccctatat gccgagcgtg gtagaaactc tggaacaaat    8160
gcaaagaaaa catggaggaa tgctagtgcg aaacccactc tcaagaaatt ccacccatga    8220
aatgtactgg gtttcatgtg aacaggaaa cattgtgtca gcagtaaaca tgacatctag    8280
aatgttgcta aatcggttca caatggctca caggaagcca acatatgaaa gagacgtgga    8340
cttaggcgct ggaacaagac atgtggcagt agaaccagag gtagccaacc tagatatcat    8400
tggccagagg atagagaata taaaaaatga acataagtca acatggcatt atgatgagga    8460
caatccatac aaaacatggg cctatcatgg atcatatgag gttaagccat caggatcggc    8520
ctcatccatg gtcaatggcg tggtgagatt gctcaccaaa ccatgggatg ttatccccat    8580
ggtcacacaa atagccatga ctgataccac acccttgga caacagaggg tgtttaaaga    8640
gaaagttgac acgcgcacac caaaagcaaa acgtggcaca gcacaaatta tggaagtgac    8700
agccaggtgg ttatggggtt tccttttctag aaacaaaaaa cccagaattt gcacaagaga    8760
ggagtttaca agaaaagtta ggtcaaacgc agctattgga gcagtgttcg ttgatgaaaa    8820
tcaatggaac tcggcaaaag aagcagtgga agacgaacgg ttctgggaac ttgtccacag    8880
agagagggag cttcataaac aggggaaatg tgccacgtgt gtctacaata tgatggggaa    8940
gagagagaaa aaattaggag agttcggaaa ggcaaaagga agtcgtgcaa tatggtacat    9000
gtggttggga gcacgcttcc tagagtttga agcccttggt ttcatgaatg aagatcactg    9060
gttcagtaga gagaattcac tcagtggagt ggaaggagaa ggactccaca aacttggata    9120
catactcaga gacatatcaa ggattccagg ggggaacatg tatgcagatg acacagccgg    9180
```

```
atgggacaca agaataacag aggatgatct ccagaatgag gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
ccagagaggc agtggacagg ttggaactta tggcttaaac actttcacca acatggaggc   9420
ccaactgata agacaaatgg agtctgaggg aatcttttta cccagcgaat tggaaacccc   9480
aaatctagcc ggaagagttc tcgactggtt ggaaaaatat ggtgtcgaaa ggctgaaaag   9540
aatggcaatc agcggagatg actgtgtggt gaaaccaatt gatgacaggt tcgcaacagc   9600
cttaacagct ttgaatgaca tgggaaaagt aagaaaagac ataccacaat gggaaccttc   9660
aaaaggatgg aatgattggc aacaagtgcc tttctgttca caccacttcc accagctaat   9720
tatgaaggat gggagggaga tagtggtgcc atgccgcaac caagatgaac ttgtggggag   9780
ggccagagta tcacaaggcg ccggatggag cctgagagaa accgcatgcc taggcaagtc   9840
atatgcacaa atgtggcagc tgatgtattt ccacaggaga gacctgagac tggcggctaa   9900
cgctatttgt tcagccgttc cagttgattg ggtcccaacc agccgcacca cctggtcgat   9960
ccatgcccat caccaatgga tgacaacaga agacatgtta tcagtatgga atagggtctg  10020
gatagaggaa aacccatgga tggaggataa gactcatgtg tccagttggg aagaagttcc  10080
atacctagga aagagggaag atcagtggtg tggatccctg ataggcttaa cagcaagggc  10140
cacctgggcc actaatatac aagtggccat aaaccaagtg agaaggctca ttgggaatga  10200
gaattatcta gattacatga catcaatgaa gagattcaag aatgagagtg atcccgaagg  10260
ggcactctgg taagtcaaca cattcacaaa ataaaggaaa ataaaaaatc aaatgaggca  10320
agaagtcagg ccagattaag ccatagtacg gtaagagcta tgctgcctgt gagccccgtc  10380
caaggacgta aaatgaagtc aggccgaaag ccacggtttg agcaagccgt gctgcctgtg  10440
gctccatcgt ggggatgtaa aaacccggga ggctgcaacc catggaagct gtacgcatgg  10500
ggtagcagac tagtggttag aggagacccc tcccaagaca caacgcagca gcggggccca  10560
acaccagggg aagctgtacc ctggtggtaa ggactagagg ttagaggaga ccccccgcgt  10620
aacaataaac agcatattga cgctgggaga gaccagagat cctgctgtct ctacagcatc  10680
attccaggca cagaacgcca gaaaatggaa tggtgctgtt gaatcaacag gttct       10735

<210> SEQ ID NO 14
<211> LENGTH: 10723
<212> TYPE: DNA
<213> ORGANISM: Dengue virus VDV2
<220> FEATURE:
<221> NAME/KEY: misc_feature
<222> LOCATION: (10361)..(10361)
<223> OTHER INFORMATION: n is a, c, g, or t

<400> SEQUENCE: 14
agttgttagt ctacgtggac cgacaaagac agattctttg agggagctaa gctcaatgta     60
gttctaacag tttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg gagaaccaca catgatcgtc    480
```

```
agcagacaag agaaagggaa aagtcttctg tttaaaacag aggttggcgt gaacatgtgt    540
accctcatgg ccatggacct tggtgaattg tgtgaagaca caatcacgta caagtgtccc    600
cttctcaggc agaatgagcc agaagacata gactgttggt gcaactctac gtccacgtgg    660
gtaacttatg ggacgtgtac caccatggga aacatagaa gagaaaaaag atcagtggca     720
ctcgttccac atgtgcgaat gggactggag acacgaactg aaacatggat gtcatcagaa    780
ggggcctgga aacatgtcca gagaattgaa acttggatct tgagacatcc aggcttcacc    840
atgatggcag caatcctggc atacaccata ggaacgacac atttccaaag agccctgatt    900
ttcatcttac tgacagctgt cactccttca atgacaatgc gttgcatagg aatgtcaaat    960
agagactttg tggaagggt ttcaggagga agctgggttg acatagtctt agaacatgga    1020
agctgtgtga cgacgatggc aaaaaacaaa ccaacattgg atttttgaact gataaaaaca    1080 gaagccaaac agcctgccac cctaaggaag tactgtatag aggcaaagct aaccaacaca    1140
acaacagaat ctcgctgccc aacacaaggg gaacccagcc taaatgaaga gcaggacaaa    1200
aggttcgtct gcaaacactc catggtagac agaggatggg gaaatggatg tggactattt    1260
ggaaagggag gcattgtgac ctgtgctatg ttcagatgca aaaagaacat ggaaggaaaa    1320
gttgtgcaac cagaaaactt ggaatacacc attgtgataa cacctcactc aggggaagag    1380
catgcagtcg gaaatgacac aggaaaacat ggcaaggaaa tcaaaataac accacagagt    1440
tccatcacag aagcagaatt gacaggttat ggcactgtca aatggagtg ctctccaaga    1500 acgggcctcg acttcaatga gatggtgttg ctgcagatgg aaaataaagc ttggctggtg    1560
cacaggcaat ggttcctaga cctgccgtta ccatggttgc ccggagcgga cacacaagag    1620
tcaaattgga tacagaarga gacattggtc actttcaaaa atccccatgc gaagaaacag    1680
gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat ccctttgag ataatggatt tggaaaaaag acatgtctta    1980
ggtcgcctga ttacagtcaa cccaattgtg acagaaaaag atagcccagt caacatagaa    2040
gcagaacctc catttggaga cagctacatc atcataggag tagagccggg acaactgaag    2100
ctcaactggt ttaagaaagg aagttctatc ggccaaatgt ttgagacaac aatgaggggg    2160
gcgaagagaa tggccatttt aggtgacaca gcctgggatt ttggatcctt gggaggagtg    2220
tttacatcta taggaaaggc tctccaccaa gtctttggag caatctatgg agctgccttc    2280 agtgggttt catggactat gaaaatcctc ataggagtca ttatcacatg gataggaatg    2340
aattcacgca gcacctcact gtctgtgaca ctagtattgg tgggaattgt gacactgtat    2400
ttgggagtca tggtgcaggc cgatagtggt tgcgttgtga ctggaaaaaa caaagaactg    2460
aaatgtggca gtgggatttt catcacagac aacgtgcaca catggacaga acaatacaar    2520
ttccaaccag aatcccccttc aaaactagct tcagctatcc agaaagccca tgaagaggac    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gcccccgaaac agcagaatgc cccaacacaa atagagcttg gaattcgttg    2880
```

```
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa atcacacac cctctggagc     3120
aatggagtgc tagaaagtga gatgataatt ccaaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac aacttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttct aacaacccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaggaaag aggattgaac caacatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtctttca aaaccaacgc cggaacaata ggtgctgtat ctctggactt ttctcctgga    4920
acgtcaggat ctccaattat cgacaaaaaa ggaaagttg tgggtcttta tggtaatggt    4980
gttgttacaa ggagtggagc atatgtgagt gctatagccc agactgaaaa aagcattgaa    5040
gacaacccag atcgaagaa tcacattttc cgaaagagaa gactgaccat catggacctc    5100
cacccaggag cggaaagac gaagagatac cttccggcca tagtcagaga agctataaaa    5160
cggggttga aacattaat cttgccccc actagagttg tggcagctga atggaggaa     5220
gcccttagag gacttccaat aagataccag acccccagcca tcagagctga gcacaccggg    5280
```

```
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460 atgcacagcca ctcccccggg aagcagagac ccatttcctc agagcaatgc accaatcata    5520
gatgaagaaa gagaaatccc tgaacgctcg tggaattccg acatgaatg ggtcacggat      5580 tttaaaggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa gaagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag agaagcaag gaaaaccttt    6120 gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac cccactggcg ctaaaagaat taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag gaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga tgggtttc      6840 ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtccta     7020 acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctcttt cttattggta gcacattatg ccatcatagg gccaggactc    7200
caagcaaaag caaccagaga agctcagaaa agagcagcgg cggcatcat gaaaaaccca   7260 actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa catagagag acgcttggag agaaatggaa agccgattg    7620 aacgcattgg gaaaaagtga attccagatc tacaagaaaa gtggaatcca ggaagtggat   7680
```

-continued

```
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggcacg aagaacccat ccccatgtca    7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt tgtccccatg   8580
gtgacacaga tggcaatgac agacacgact ccatttggac aacagcgcgt ttttaaagag   8640
aaagtggaca cgagaaccca agaaccgaaa gaaggcacga gaaactaat gaaaataaca    8700 gcagagtggc tttggaaaga attagggaag aaaaagacac caggatgtg caccagagaa    8760 gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg aaggagaag ggctgcacaa gctaggttac   9120
attctaagag acgtgagcaa gaaagaggga ggagcaatgt atgccgatga caccgcagga   9180
tgggatacaa aaatcacact agaagaccta aaaaatgaag aratggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtgacaagt tggcacctat ggactcaata ctttcaccaa tatggaagcc    9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca taacaatgg gaaccttca     9660 agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aaacatggga ggaaatccca  10080
```

```
tacttgggga aaagagaaga ccaatggtgc ggctcattga ttgggttaac aagcagggcc   10140
acctgggcaa agaacatcca agcagcaata aatcaagtta gatcccttat aggcaatgaa   10200
gaatacacag attacatgcc atccatgaaa agattcagaa gagaagagga agaagcagga   10260
gttctgtggt agaaagcaaa actaacatga aacaaggcta gaagtcaggt cggattaagc   10320
catagtacgg aaaaaactat gctacctgtg agccccgtcc naggacgtta aaagaagtca   10380
ggccatcata aatgccatag cttgagtaaa ctatgcagcc tgtagctcca cctgagaagg   10440
tgtaaaaaat ccgggaggcc acaaaccatg gaagctgtac gcatggcgta gtggactagc   10500
ggttagggga gacccctccc ttacaaatcg cagcaacaat gggggcccaa ggcgagatga   10560
agctgtagtc tcgctggaag gactagaggt tagaggagac cccccgaaa caaaaaacag   10620 catattgacg ctgggaaaga ccagagatcc tgctgtctcc tcagcatcat tccaggcaca   10680
gaacgccaga aaatggaatg gtgctgttga atcaacaggt tct                    10723
```